(12) United States Patent
Engelhardt et al.

(10) Patent No.: US 7,220,854 B1
(45) Date of Patent: May 22, 2007

(54) SUGAR MOIETY LABELED NUCLEOTIDE, AND AN OLIGO- OR POLYNUCLEOTIDE, AND OTHER COMPOSITIONS COMPRISING SUCH SUGAR MOIETY LABELED NUCLEOTIDES

(75) Inventors: Dean Engelhardt, New York, NY (US); Elazar Rabbani, New York, NY (US); Stanley Kline, Brooklyn, NY (US); Jannis G. Stavrianopoulos, New York, NY (US); Dollie Kirtikar, Elmhurst, NY (US)

(73) Assignee: Enzo Life Sciences, Inc. c/o Enzo Biochem, Inc., Farmingdale, NY (US)

( * ) Notice: Subject to any disclaimer, the term of this patent is extended or adjusted under 35 U.S.C. 154(b) by 0 days.

(21) Appl. No.: 08/486,066

(22) Filed: Jun. 7, 1995

Related U.S. Application Data

(60) Continuation of application No. 07/960,071, filed on Oct. 13, 1992, now abandoned, which is a continuation of application No. 07/531,953, filed on Jun. 1, 1990, now abandoned, which is a division of application No. 07/140,980, filed on Jan. 5, 1988, now abandoned, which is a continuation of application No. 06/674,352, filed on Nov. 21, 1984, now abandoned, which is a continuation of application No. 06/391,440, filed on Jun. 23, 1982, now abandoned.

(51) Int. Cl.
    *C07H 19/04* (2006.01)
(52) U.S. Cl. ..................................... 536/26.1
(58) Field of Classification Search .................... 435/6, 435/810; 436/501; 536/22.1, 23.1, 24.1, 536/24.3–24.33, 25.3; 935/77, 78
See application file for complete search history.

(56) References Cited

U.S. PATENT DOCUMENTS

| | | |
|---|---|---|
| 3,931,397 A | 1/1976 | Harnden |
| 3,960,840 A | 6/1976 | Secrist, III et al. |
| 4,038,480 A | 7/1977 | Robins et al. |
| 4,124,702 A | 11/1978 | Lampson et al. |
| 4,213,893 A | 7/1980 | Carrico et al. |
| 4,230,797 A | 10/1980 | Boguslaski et al. |
| 4,255,566 A | 3/1981 | Carrico et al. |
| 4,260,737 A | 4/1981 | Scherberg |
| 4,310,662 A | 1/1982 | Crea |
| 4,313,938 A | 2/1982 | Arimura et al. |
| 4,358,535 A | 11/1982 | Falkow et al. |
| 4,378,458 A | 3/1983 | Gohlke et al. |
| 4,443,594 A | 4/1984 | Buckmann |
| 4,460,772 A | 7/1984 | Benovic et al. |
| 4,581,333 A | 4/1986 | Kourilsky et al. |
| 4,605,735 A | 8/1986 | Miyoshi et al. |
| 4,707,440 A | 11/1987 | Stavrianopoulos |
| 4,708,935 A | 11/1987 | Suhadolnik et al. |
| 4,711,955 A | 12/1987 | Ward et al. |
| 4,828,979 A | 5/1989 | Klevan et al. |
| 4,833,251 A | 5/1989 | Musso et al. |
| 4,880,918 A | 11/1989 | Rapaport |
| 5,260,433 A * | 11/1993 | Engelhardt et al. ........ 536/23.1 |

FOREIGN PATENT DOCUMENTS

| | | |
|---|---|---|
| DE | A-25-07-901 | 9/1970 |
| DE | A-18-14-134 | 1/1971 |
| DE | A-16-17-886 | 9/1976 |
| DE | 2915082 A1 | 10/1979 |
| DE | 2915082 C2 | 7/1989 |

(Continued)

OTHER PUBLICATIONS

Kropinksi, et al., "Isolation and Properties of a *Pseudomonas-acidovrans* Bacteriophage," *J. Gen. Virol.*, 6:85-93 (1970).

(Continued)

*Primary Examiner*—John S. Brusca
(74) *Attorney, Agent, or Firm*—Ronald C. Fedus

(57) ABSTRACT

The present invention provides a nucleotide having the formula,

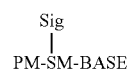

wherein PM is a phosphate moiety, SM is a ribose or a deoxyribose sugar moiety, and BASE is a pyrimidine, purine or 7-deazapurine moiety. PM is attached to SM at a position independently selected from the 2', 3', and 5' positions of SM when the nucleotide is a ribonucleotide, and at a position independently selected from the 3' and 5' positions when the nucleotide is a deoxyribonucleotide. BASE is attached to the 1' position of SM from the $N^1$ position when BASE is a pyrimidine, or the $N^9$ position when BASE is a purine or 7-deazapurine. Sig is a detectable moiety covalently attached to SM directly or through a linkage group. Also provided are an oligo- or polynucleotide comprising at least one such sugar moiety labeled nucleotide, and other compositions including those wherein a polypeptide is terminal ligated or attached to the oligo- or polynucleotide. The sugar moiety labeled nucleotide, and the oligo- or polynucleotides and other compositions comprising such nucleotides, are useful as diagnostic tools for detecting analytes and as therapeutic agents.

33 Claims, 4 Drawing Sheets

FOREIGN PATENT DOCUMENTS

| | | |
|---|---|---|
| EP | 0 027 631 B1 | 5/1982 |
| EP | O 061 760 A1 | 10/1982 |
| EP | O 061 761 A1 | 10/1982 |
| EP | O 061 762 A2 | 10/1982 |
| EP | 0 169 787 A1 | 1/1986 |
| EP | 0 225 807 A2 | 6/1987 |
| EP | 0 063 879 B1 | 11/1989 |
| GB | 2 019 408 A | 10/1979 |
| GB | 2 036 029 A | 6/1980 |
| GB | 2 040 943 A | 9/1980 |
| JP | 53-133283 | 11/1978 |
| JP | 57-11999 | 1/1982 |
| JP | 60-96610 | 5/1985 |
| JP | 60-169495 | 9/1985 |
| JP | 57-42632 | 3/1986 |
| JP | 61-103824 | 5/1986 |
| SU | A 659 573 | 4/1979 |
| WO | WO 83/02276 | 7/1983 |
| WO | WO 83/02277 | 7/1983 |
| WO | WO 86/02929 | 5/1986 |

OTHER PUBLICATIONS

Bhat, C.C., "Preparation of a Crystalline O-Acyl-2-deoxypentofuranosyl Halide," *Synthetic Procedures in Nucleic Acid Chemistry*, vol. 1. *Preparation of Purines, Pyrimidines, Nucleosides, and Nucleotides*, (Zorbach, W.W. et al., Eds.), Interscience Publishers, John Wiley & Sons, Inc., N.Y., 1968, pp. 521-522.

Caruthers, M.H., "The Role of Synthetic DNA in Recombinant DNA Research," *DNA* 1(2): 166-167 (1982), from Second Annual Congress for Recombinant DNA Research, Los Angeles, 1982.

Becker et al., "Irreversible Inhibition of Biotin Transport in Yeast by Biotinyl-p-nitrophenyl Ester," *Proc. Nat'l. Acad. Sci. (USA)* 68:2604-2607 (1971)[1] [Exhibit 1].

Halloran et al., "The Preparation of Nucleotide-protein Conjugates: Carbodiimldes as Coupling Agents," *J. Immunol.*, 96:373-378 (1966)[1] [Exhibit 2].

Manning et al., "A New Method of in situ Hybridization," *Chromosoma*, 53:107-117 (1975)[1] [Exhibit 3].

Kropinski et al., *Gen. Virol.*, 6:85 (1970)[1,5] [Exhibit 4].

Kropinski et al., "5-(4-Aminobutylaminomethyl) uracil, An Unusual Pyrimidine from the Deoxyribonucleic Acid of Bacteriophage ΦW-14," *Biochemistry*, 12:151-157 (1973)[1] [Exhibit 5].

Bhat, *Syn. Proc. in Nucleic Acid Chem.*, vol. I., p. 521 (1968)[1,5] [Exhibit 6].

Torrence et al., "5-0-Alkylated Derivatives of 5-Hydroxy-2'-deoxyuridine as Potential Antiviral Agents. Anti-Herpes Activity of 5-Propynyloxy-2'-deoxyuridine," *J. Med. Chem.*, 21:228-231 (1978)[1] [Exhibit 7].

Michelson, "Synthesis Of Nucleotide Anhydrides By Anion Exchange," *Biochem. Biophys. Acta.*, 91:1-13 (1964)[1] [Exhibit 8].

Cech et al. "A facile synthesis of 5-(perfluoroalkyl)-pyrimidines," *Nucl. Acids Res.*, 2:2183-2192 (1979)[1] [Exhibit 9].

Schram et al., "Pyrrolopyrimidine Nucleosides VIII. Synthesis of Sangivamycin Derivatives Possessing Exocyclic Heterocycles at C5," *J. Carbohydrate, Nucleosides, Nucleotides*, 1:39-54 (1974)[1] [Exhibit 10].

Bleackley et al., "The preparation of 5-cyanouracil and 5-cyano-2'-deoxyuridine from the corresponding 5-iodo derivative and cuprous cyanide," *Nucl. Acids Res.*, 2:683-690 (1975)[1] [Exhibit 11].

Roberts et al., "Uridine and Cytidine Derivatives," *J. Am. Chem Soc.* 74:668-669 (1952)[1] [Exhibit 12].

Bauman et al., "Rapid and High Resolution Detection of in situ Hybridisation to Polytene Chromosomes Using Fluorochrome-labeled RNA," *Chromosoma*, 84:1-18 (1982)[1] [Exhibit 13].

Bauman et al., "A new method for fluorescence microscopical localization of specific DNA sequences by in situ hybridization of fluorochrome-labelled RNA," *Exp. Cell Res.*, 128:485-490 (1980)[1] [Exhibit 14].

Gerhard et al., "Localization of a Unique Gene by Direct Hybridization in situ," *Proc. Natl. Acad. Sci. ( USA)*, 78:3755-3759 (1981)[1] [Exhibit 15].

Miller, J., "Experiment 52, Assay of the Iac Repressor by Binding to Operator," *Experiments in Molecular Genetics*, Cold Spring Harbor Laboratory pp. 367-370 (1972)[1] [Exhibit 16].

Ueda et al., "Conversion of Uridine Nucleotides to the 6-Cyano Derivatives: Synthesis of Orotidylic Acid (Nucleosides and Nucleotides)," *J. Carbohydr., Nucleosides, Nucleotides*, 5:261-271 (1978)[1] [Exhibit 17].

Brunngraber et al., "Purification and Properties of a Nucleoside Phosphotransferase from Carrot," *J. Biol. Chem.*, 242:4834-4840 (1967)[1] [Exhibit 18].

Wilchek et al., "Modification of the Carboxyl Groups of Ribonuclease by Attachment of Glycine or Alanyglycine," *Biochemistry*, 6:247-252 (1967)[1] [Exhibit 19].

Vogt, "Purification and Properties of $S_1$ Nuclease from Aspergillus," *Methods in Enzymology*, 65:248-255 (1980)[1] [Exhibit 20].

Monod et al., "On the Nature of Allosteric Transitions: A Plausible Model," *J. Mol. Biol.*, 12:88-118 (1965)[1] [Exhibit 22].

Pastan et al., "Cyclic Adenosine Monophosphate in Bacteria," *Science*, 169:339-344 (1969)[1] [Exhibit 23].

Gilbert et al., "The Nucleotide Sequence of the Iac Operator," *Proc. Natl. Acad. Sci. (USA)*, 70:3581-3584 (1973)[1] [Exhibit 24].

Pardee, "Membrane Transport Proteins," *Science*, 162:632-637 (1968)[1] [Exhibit 25].

Hazelbaur et al., "Role of the Galactose Binding Protein in Chemotaxis of *Escherichia coli* toward Galactose," *Nature New Bio.*, 230:101-104 (1971)[1] [Exhibit 26].

Caruthers, Second Annual Congress for Recombinant DNA Research, Los Angeles, CA (1982)[1,5] [Exhibit 27].

Langer et al., "Enzymatic synthesis of biotin-labeled polynucleotides: Novel nucleic acid affinity probes," *Proc. Natl. Acad. Sci. (USA)*, 78:6633-6637 (1981)[2,4,9,18,22] [Exhibit 40].

Nishimura et al., "Synthetic Nucleosides and Nucleotides. XV. 1) 5-Dimethylamino-2-oxidoisoquinolln-1-yl Diazomethane: A Novel Water-Soluble Fluorescent Labelling Agent for Nucleotides," *Chem. Pharm Bull.*, 28:1695-1703 (1980)[2,4] [Exhibit 41].

Kwah et al., "Myocardinal Infarct Imaging of Antibodies to Canine Cardiac Myosin with Indium-111-Diethylenetriamine Pentaacetic Acid," *Science* 209:295-297 (1980)[3] [Exhibit 42].

Torrence et al., "Interferon Inducers: General Survey and Classification," *Methods in Enzymology*, vol. 78, Interferons, Part A, pp. 291-299 (Pestka, Edu.), Academic Press, New York, 1981[10] [Exhibit 44].

Siebenlist et al., "Contacts between *Escherichia coli* RNA polymerase and an early promoter of phage T7," *Proc. Natl. Acad. Sci. (USA)*, 77:122-126, Jan. 1980[17] [Exhibit 53].

Maxam et al., "A New Method for Sequencing DNA," *Proc. Natl. Acad. Sci. (USA)*, 74:560-564, 1977[17] [Exhibit 54].

Heggeness et al., "Avidin Binds To Condensed Chromatin," *Stain Technol.* 52:165-169 (1977)[18] [Exhibit 55].

Heggeness et al., "Use of the Avidin-Biotin Complex For the Localization of Actin and Myosin with Fluorescence Microscopy," *J. Cell Biol.* 73:783-788 (1977)[18] [Exhibit 56].

Bayer et al., "The Use of the Avidin-Biotin Complex as a Tool in Molecular Biology," *Methods of Biochem Analysis* 26:1-45 (1980)[18] [Exhibit 57].

Hoffman et al., "Iminobiotin affinity columns and their application to retrieval of streptavidin," *Proc. Natl. Acad. Sci. 77*:4666-4668 (1980)[18] [Exhibit 58].

Pardue et al, "Nucleic Acid Hybridization to the DNA of Cytological Preparations," *Methods in Cell Biol.* 10:1-16 (1975)[18] [Exhibit 59].

Bergstrom et al., "C-5 Substituted Pyrimidine Nucleosides. 2. Synthesis via Olefin Coupling to Organopalladium Intermediates Derived from Uridine and 2'-Deoxyuridine," *JACS 100*:8106-8112 (1978)[Exhibit 60].

Bigge et al., "Palladium-Catalyzed Coupling Reactions of Uracil Necleosides and Nucleotides," *JACS 102*:2033-2038 (1979)[18] [Exhibit 61].

Rigby et al., "Labeling Deoxyribonucleic Acid to High Specific Activity in Vitro by Nick Translation with DNA Polymerase I," *J. Mol. Biol. 113*:237-251 (1977)[18] [Exhibit 62].

Bourguignon et al., "DNA of Minute Virus of Mice:Self-Priming, Nonpermutated Single-Stranded Genome with a 5'-Terminal Hairpin Duplex," *J. Virol. 20*:290-306 (1976)[18] [Exhibit 63].

Miller et al., "A general method for permeabilizing mono-layer and suspension cultured animal cells," *Exp. Cell Res. 120*:421-425 (1979)[18] [Exhibit 64].

Schulman et al., "Attachment of protein affinity-labeling reagents of variable length and amino acid specificity to *E. coli* tRNA$^{FMt1}$," *Nuc. Acid Res. 9*:1203-1217, (1981)[25] [Exhibit 77].

Langer, et al., "Enzymatic synthesis of biotin-labeled polynucleotides: Novel nucleic acid affinity probes," *Chemical Abstracts*, vol. 96, No. 7, Feb. 15, 1982, p. 207, *Abstract No. 47771z*[4, 21] [Exhibit 78].

Clechet, P. et al., "Trace analysis of barium in water means of cation resin-loaded paper and x-ray fluorescence analysis," *Chemical Abstracts*, vol. 94, No. 25, Jun. 22, 1981, p. 366, *Abstract No. 214298t*[4] [Exhibit 79].

Duke et al., "Conformational change accompanying modification of myosin ATPase," *Chemical Abstracts*, vol. 66, No. 9, Feb. 27, 1967, p. 3326, *Abstract No. 35045h*[4] [Exhibit 80].

Duke et al., "Conformational change accompanying modification of myosin ATPase," *Biochem. Biophys. Acta,* 126:600-603 (1966)[4] [Exhibit 81].

Kathawala et al., "Darstellung von Desoxy-oligonucleotiden Mit 2'.3'-[2.4-Dimethoxy-benzyliden]-uridin als Phosphat-Schutzgruppe," *Lieblgs Ann. Chem.,* 712:195-200 (1968)[4, 27] [Exhibit 84].

Trouet et al., "Targeting of antitumor and antiprotozoal drugs by covalent linkage to protein carriers," *Chemical Abstracts*, vol. 98, No. 9, Feb. 28, 1983, pp. 334-335, Abstract No. 77997m[4] [Exhibit 85].

Trouet et al., "Targeting of antitumor and antiprotozoal drugs by covalent linkage to protein carriers," *NATO Adv. Study Inst. of Targeting of Drugs. Series A, Life Sciences,* 47:19-30, Plenum Press NY (1981)[4] [Exhibit 86].

Angerer et al., "An Electron Microscope Study of the Relative Positions of the 4S and Ribosomal RNA Genes in HeLa Cell Mitochondrial DNA," *Cell 9*:81-90 (1976)[4] [Exhibit 89].

Mackey et al., "Preparation and Characterization of Highly Radioactive in Vitro Labeled Adenovirus DNA and DNA Restriction Fragments," *Biochemistry,* 16:4478-4482 (1977)[4] [Exhibit 91].

Zhenodarova et al., "Spin-labeled Derivatives of Oligoribonucleotides as Spin Probes for Studying the Mechanism of the Effect of Enzymes," *Chemical Abstracts*, vol. 91, 1979, p. 303, Abstract No. 85951n[4] [Exhibit 92].

Salam et al., "Synthesis of Nucleoside 5'-(β-D-Glucopyranosyl Monophosphates) by the Sugar Ortho Ester Route," *Carbohydrate Research,* 102:139-149 (1982)[4] [Exhibit 95].

Salam et al., "Synthesis of Acetylated α-and β-L-Fucosyl Esters of Nucleoside 5'-Monophosphates by the Orthoester Route," *Nucleotides & Nucleosides,* 1:155-161 (1982)[4] [Exhibit 96].

Kochetkov, N.K. and Budovskii, E.I. Editors, *Organic Chemistry of Nucleic Acids, Part B*, Chapter 9, pp. 449-476, Plenum Press, Londan and New York (1972).

Armgstrong, V.W. and Eckstein, R., *Eur. J. Biochem* 70:33-38 (1976).

Rozovskaya T.A. et al., *Molekulyarnaya Biologiya* 11(3):598-610 (1977).

Petrov, A.I. and Sikhourukov B.I., *Nucleic Acids Research* 8(*18*):4221-4234 (1980).

Petrov,,A.I., *Nucleic Acids Research* 8(*223*):5931-5929 (1980).

Hiratsuka T., and Uchida, K., *Biochemica et Biophysica Acta 320*:365-647 (1973).

Bauman, J.G.J. et al., *J. Histochem. Cytochem.* 29:227-237 (1981).

Broker, T.R. et al., *Nucleic Acid Research* 5(*2*):363-384 (1978).

Sodja, A. and Davidson, N., *Nucleic Acid Research* 5(*2*):385-401 (1978).

Daniel, F.B. and Beerman, E.J. *Biochemistry* 15:565-568 (1976).

Eberhard W. et al., *Nucleic Acids Research Symposium Series Exhibit* 9:15-19 (1981).

Saffhil, R., and Hall, J.J., *Carbohydrates Nucleosides Nucleotides* 8:573-583 (1981).

Erlanger, B.F. et al., *Proc. Natl. Acad. Sci.* 52:68-74 (1964).

Suzuki S. et al., *Bioinorganic Chemistry* 3:281-293 (1974).

Manning, J. et al., *Biochemistry* 16(*7*):1364-1370 (1977).

Avramess S., *Immunochemistry,* vol. 6:43-52 (1969).

\* cited by examiner

FIG. 3A  DNA BINDING TO CON A SEPHAROSE EFFECT ON MANNOSE

SUGAR MOIETY LABELED NUCLEOTIDE, AND AN OLIGO- OR POLYNUCLEOTIDE, AND OTHER COMPOSITIONS COMPRISING SUCH SUGAR MOIETY LABELED NUCLEOTIDES

CROSS-REFERENCE TO OTHER RELATED APPLICATIONS

This application is a continuation of U.S. patent application Ser. No. 07/960,071, filed on Oct. 13, 1992, now abandoned, which is a continuation of U.S. patent application Ser. No. 07/531,953, filed on Jun. 1, 1990, also abandoned, which is a division of U.S. patent application Ser. No. 07/140,980, filed on Jan. 5, 1988, abandoned, which is a continuation of Ser. No. 06/674,352, filed Nov. 21, 1984, abandoned, which is a continuation of U.S. application Ser. No. 06/391,440, filed on Jun. 23, 1982, abandoned. Two divisional applications of the aforementioned Ser. No. 07/140,980, U.S. patent application Ser. No. 07/532,704 (filed on Jun. 4, 1990) for "Base Moiety Labeled Detectable Nucleotide" and Ser. No. 07/567,039 (filed on Aug. 13, 1990) for "Saccharide Specific Binding System Labeled Nucleotides" issued as U.S. Pat. No. 5,241,060 (Aug. 31, 1993) and U.S. Pat. No. 5,260,433 (Nov. 9, 1993), respectively.

BACKGROUND OF THE INVENTION

It is known to produce nucleotides or polynucleotides which are radioactively labeled, such as with isotopes or hydrogen ($^3$H), phosphorus ($^{32}$P), carbon ($^{14}$C) or iodine ($^{125}$I). Such radioactively labeled compounds are useful to detect, monitor, localize and isolate nucleic acids and other molecules of scientific or clinical interest. Unfortunately, however, the use of radioactively labeled materials presents hazards due to radiation. Also due to the relatively short half life of the radioactive materials employed to label such compounds or materials, the resulting labeled compounds or materials have a corresponding relatively short shelf life.

It has been proposed to chemically label compounds of interest, such as nucleotides and polynucleotides, so as to overcome or avoid the hazards and difficulties associated with such compounds or materials when radioactively labeled. In the article by P. R. Langer, A. A. Waldrop and D. C. Ward entitled "Enzymatic Synthesis of Biotin-Labeled Polynucleotides: Novel Nucleic Acid Affinity Probes", in *Proc. Natl. Acad. Sci.*, USA, Vol. 78, No. 11, pp. 6633–6637, November, 1981, there are described analogs of dUTP and UTP that contain a biotin molecule bound to the C-5 position of the pyrimidine ring through an alkylamine linker arm. The biotin-labeled nucleotides are efficient substrates for a variety of DNA and RNA polymerases in vitro. Polynucleotides containing low levels of biotin substitution (50 molecules or fewer per kilobase) have denaturation, reassociation and hybridization characteristics similar to those of unsubstituted controls. Biotin-labeled polynucleotides, both single and double stranded, are selectively and quantitatively retained on avidin-Sepharose, even after extensive washing with 8M urea, 6M guanidine hydrochloride or 99% formamide. In addition, biotin-labeled nucleotides can be selectively immunoprecipitated in the presence of antibiotin antibody and *Staphylococcus aurea*, Protein A. These unique features of biotin-labeled polynucleotides suggest that they are useful affinity probes for the detection and isolation of specific DNA and RNA sequences. It is indicated in the article that the subject matter of the article is comprised in a pending U.S. patent application.

The disclosures of this article and above-referred pending patent application are herein incorporated and made part of this disclosure.

The patent application referred to in the above-identified article is U.S. patent application Ser. No. 255,223 filed Apr. 17, 1981. Ser. No. 06/225,223 was abandoned in favor of continuation application, U.S. patent application Ser. No. 06/496,915, filed on May 23, 1983, now U.S. Pat. No. 4,711,955. A related divisional application of the aforementioned Ser. No. 06/496,915 was filed as U.S. patent application Ser. No. 07/130,070 (on Dec. 8, 1987), and has sinced issued on Jul. 12, 1994 as U.S. Pat. No. 5,328,824. Two related continuation applications of the aforementioned Ser. No. 07/130,070 were filed on Feb. 26, 1992 (as Ser. No. 07/841,910) and on May 20, 1992 as (Ser. No. 07/886,660). The former, Ser. No. 07/841,910, has been allowed, and the latter, Ser. No. 07/886,660, issued as U.S. Pat. No. 5,449,767, on Sep. 12, 1995. Therefore, the disclosures of all three aforementioned U.S. Pat. Nos. 4,711,955, 5,328,824 and 5,449,767 are herein incorporated by reference and made part of the instant disclosure. The disclosures of this pending U.S. patent application Ser. No. 255,223 are herein incorporated and made part of this disclosure. In the above-identified pending U.S. patent application the subject matter of the above-identified article is disclosed and additionally it is disclosed that compounds having the structure:

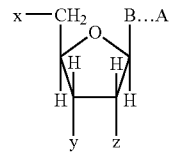

wherein B represents a purine, deazapurine, or pyrimidine moiety covalently bonded to the $C^{1'}$-position of the sugar moiety, provided that when B is purine or 7-deazapurine, it is attached at the $N^9$-position of the purine or deazapurine, and when B is pyrimidine, it is attached at the $N^1$-position;

wherein A represents a moiety consisting of at least three carbon atoms which is capable of forming a detectable complex with a polypeptide when the compound is incorporated into a double-stranded ribonucleic acid, deoxyribonucleic acid duplex, or DNA-RNA hybrid;

wherein the dotted line represents a chemical linkage joining B and A, provided that if B is purine the linkage is attached to the 8-position of the purine, if B is 7-deazapurine, the linkage is attached to the 7-position of the deazapurine, and if B is pyrimidine, the linkage is attached to the 5-position of the pyrimidine; and wherein each of x, y, and z represents

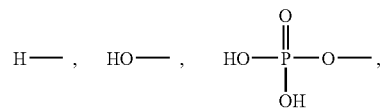

-continued

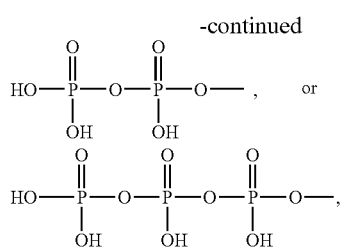

are widely useful as probes in biomedical research and recombinant DNA technology.

Particularly useful are compounds encompassed within this structure which additionally have one or more of the following characteristics: A is non-aromatic; A is at least $C_5$; the chemical linkage joining B and A includes an .alpha.-olefinic bond; A is biotin or iminobiotin; and B is a pyrimidine or 7-deazapurine.

The publications cited in the aforementioned U.S. Pat. Nos. 4,711,955, 5,328,824, and 5,449,767 are also herein incorporated and made part of this disclosure.

SUMMARY OF THE INVENTION

In accordance with the practices of this invention nucleotides are modified, such as at the 5 position of pyrimidine or the 7 position of purine, preparatory for the preparation therefrom of nucleotide probes suitable for attachment to or incorporation into DNA or other nucleic acid material. In the practices of this invention nucleotides, i.e. nucleic acids, preferably are modified in a non-disruptive manner such that the resulting modified nucleotides are capable of incorporation into nucleic acids and once incorporated in nucleic acids the modified nucleotides do not significantly interfere with the formation or stabilization of the double helix formed of the resulting nucleic acids containing the modified nucleotides. The non-disruptive modification of nucleotides and nucleic acids incorporating such modified nucleotides is in contrast with those modifications of nucleotides which are characterized as a disruptive modification in the sense that the resulting disruptively modified nucleotides and nucleic acids containing the same block proper double helix formation. In the practices of this invention, the nucleotides are desirably modified at the 5 position of the pyrimidine or the 7 position of the purine. The nucleotides so modified are non-disruptively modified and nucleic acids containing such nucleotides are capable of forming a double helix arrangement.

Broadly, in another aspect of the practices of this invention various methods are useful for the tagging or labeling of DNA in a non-disruptive manner. For example, biotin is added on the end of a DNA or RNA molecule. The addition of biotin is accomplished by addition of a ribonucleotide. The 3', 4' vicinal hydroxyl groups are oxidized by periodate oxidation and then reduced by a borohydride in the presence of biotin hydrazide.

Alternatively, carbodiimide can also be used to couple biotin to the aldehyde group. Another technique for tagging nucleic acid material such as DNA or RNA involves the addition of a large marker to the end of a DNA or RNA molecule. One example of this technique is the addition of a molecule, e.g. lysylglycine, where the amino groups are tagged with biotin. Another example would be to follow the procedure set forth hereinabove but employing carbodiimide as the cross-linking agent. Still another example of this technique would be to produce a biotinylated dA:dU double helical polymer and to ligate this polymer to the probe prepared in accordance with this invention.

Another technique for tagging DNA in a non-disruptive manner involves the isolation of dPyrTP having a putricine or spermidine on the 5 position from PS16 or phage-infected cells. If desired, dPyrTP is made from phage DNA and phosphorylated to dPyrTP followed by modification of the polyamine side chain by means of standard nucleophilic reagent NHS-biotin.

Another technique for tagging DNA in a non-disruptive manner involves the addition of glucose to 5-hydroxymethylcytosine (5 HMC) in DNA using T4 phage glycoslyating enzymes followed by screening by means of a lectin-based assay.

Still another method for tagging DNA in a non-disruptive manner involves 5-HMC-triphosphate made from the hydrolysis of T4-DNA followed by phosphorylation of the 5HMCMP to 5 HMCTP. 5HMCTP is then incorporated into DNA using polymerase I. Thus, any DNA can be modified to have non-disruptively incorporated therein 5 HMC.

A method for tagging DNA in a mildly disruptive manner involves reacting nucleic acids in the double helical form with alkylating reagents as for example benz(o)pyrene diol epoxide or aflatoxin. Under appropriate conditions the $N^2$ group of guanine, the $N^4$ group of adenosine or the $N^4$ group of cytosine are alkylated. These modified nucleotides can be directly detected with antibodies or can be used as linking arms for the addition of a reporter molecule such as biotin.

BRIEF DESCRIPTION OF DRAWINGS

FIG. 3A is a graph that illustrated the recovery (measured as a percent) of tritium-labeled T4 DNA using a Con A-sepharose column when mannose is included in the buffer, as described in Example XXII.

Figure 1:
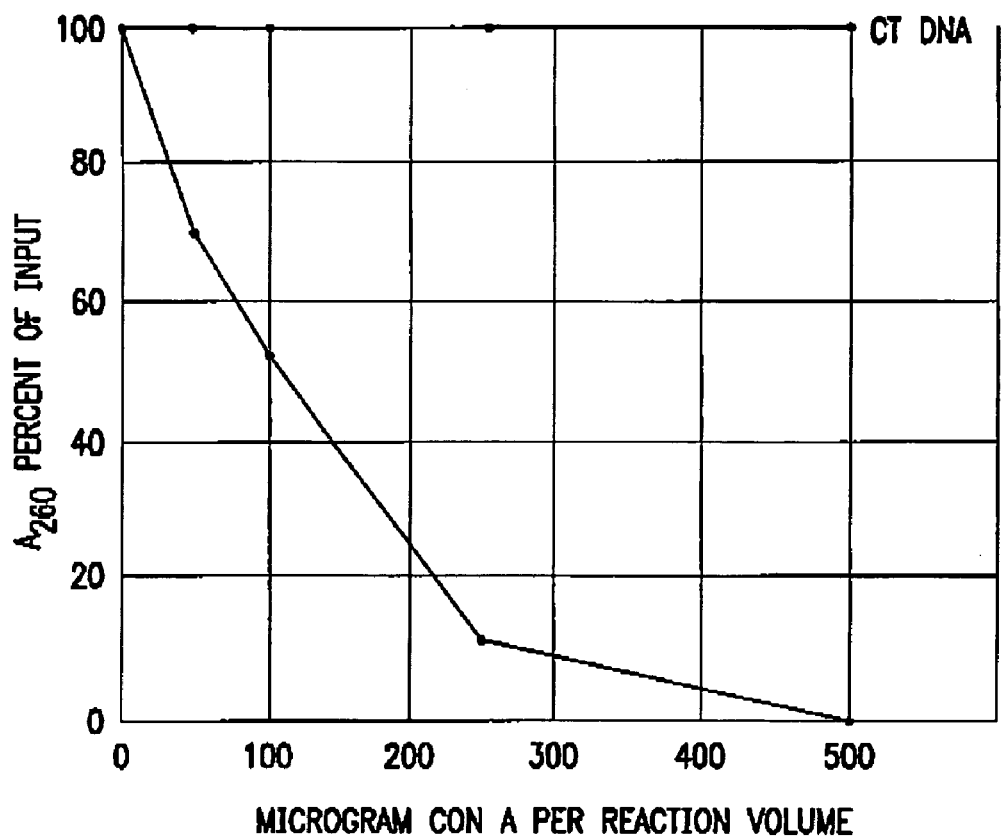
FIG. 1 is a graph that shows the results of a precipitation reaction of glucosylated DNA as described in Example XXI. Absorbance was measured at 260 nanometers for the reaction mixtures and control solutions.

The following examples are illustrative of various embodiments of the practices of this invention:

EXAMPLE I

Biotinyl-N-hydroxysuccinide ester (BNHS) was prepared according to a method of Becker et al, P.N.A.S. 68 2604

(1971). Biotin (0.24 g, 1.0 mmol) was dissolved in 5 ml dry dimethylformamide. Dicyclohexylcarbodimide (0.21 g, 1.0 mmol) and N-hydroxysuccinimide (0.12 g, 1.0 mmol) were added and the solution stirred at room temperature for 15 hours. After filtration of the subsequent precipitate, the filtrate was evaporated at reduced pressure the residue was washed twice with ethanol and recovered from hot isopropyl alcohol to yield a white crystalline product having a m.p. of 216°–218° C.

EXAMPLE II

Biotinyl-1,6-diaminohexane amide was prepared as follows: A solution of 1,6-diaminohexane (320 mg, 2.0 mmol), dissolved in 50 ml water, was brought to pH 8.5 by addition of carbon dioxide. Biotinyl-N-hydroxysuccinimide ester (100 mg, 0.29 mmol), dissolved in 10 ml dimethylformamide, was added. After 18 hours at room temperature the mixture was evaporated and the residue washed with ether and subsequently dried in a dessicator.

EXAMPLE III

Polybiotinylated poly-L-lysine was prepared by the following procedure. Polylysine (100 umol lysine) dissolved in 2 ml 0.1 M sodium borate, pH 8.5 was added to biotinyl-N-hydroxysuccimide ester (17.5 mg, 50 umol) dissolved in 0.5 ml dimethylformamide. After stirring at room temperature for 18 hours, the mixture was dialyzed against 10 mM tris buffer, pH 7.5.

EXAMPLE IV

Oligodeoxyribonucleotides were end-labeled using cytidine-5'-triphosphate and terminal transferase as follows. Purified phase DNA, alkali sheared with 0.2 N sodium hydroxide and diluted to 2 $A_{260}$ units/ml in potassium cacodylate (0.1 M), tris base (25 mm), cobalt chloride (1 mM) and dithiothreitol (0.2 M) were used. To this DNA solution (1 ml) was added cytidine-5'-triphosphate (10 mmol) and terminal transferase (200 units).

After incubating at 37° for 5 to 8 hours the reaction was stopped by the addition of neutralized phenol (100 ul), 0.5M EDTA (100 ul) and 1% sodium dodecyl sulfate (100 ul). The DNA was purified by gel filtration chromatography through Sephadex G-100 followed by precipitation with ethanol.

EXAMPLE V

Biotin and polybiotinylated poly-L-lysine were coupled to oligoribonucleotides using a carbodimide coupling procedure described by Halloran and Parker, *J. Immunol.*, 96 373 (1966). As an example, DNA (1 ug/ml), 1 ml) in tris buffer pH 8.2, sheared with 0.1 N sodium hydroxide was denatured by boiling for 10 minutes and quick cooling in an ice bath. Biotinyl-1,6-diaminohexane amide (2 mg, 6 umol) or polybiotinylated poly-L-lysine (2 mg) and 1-ethyl-3-diisopropylaminocarboimide HCl (10 mg, 64 umol) were added, and the pH readjusted to 8.2. After 24 hours at room temperature in the dark, the mixture was dialyzed against 10 mM tris buffered saline. DNA was precipitated ethanol.

EXAMPLE VI

Biotin, conjugated to cytochrome C, was prepared by the following procedure. To a solution of cytochrome C (10 mg) in 1 ml of 0.1 M sodium borate, pH 8.5 was added biotinyl-N-hydroxysuccinimide ester (10 mg, 29 umol) in 1 ml dimethyl formamide. After 4 hours at room temperature, the biotinylated protein was purified by gel filtration chromatography through a Sephadex G-50 column.

EXAMPLE VII

Formaldehyde coupling of cytochrome C-biotin and polybiotinylated poly-L-lysine to oligodeoxyribonucleotides were carried out using a method similar to that described by Manning et al, *Chromosoma*, 53, 107 (1975). Oligodeoxyribonucleotide fragments obtained by sodium hydroxide shearing of purified DNA (100 ug/ml in 10 mM triethanolamine, pH 7.8 were denatured by boiling for 10 minutes followed by quick cooling in ice. Cytochrome C-biotin 0.05 g ml or polybiotinylated poly-L-lysine solution (0.05 ml) dissolved 3 mg/ml in 10 mM triethanolamine, pH 7.8 was added to 1 ml at the denatured oligodeoxyribonucleotide solution along with 0.1 ml of 6% formaldehyde in 10 mM triethanolamine, pH 7.8. After stirring at 40° for 30 minutes the mixture was dialyzed against the same buffer. The oligodeoxyribonucleotidebiotin complex was finally purified by gel filtration chromatography on Sephadex G-100 followed by precipitation from ethanol.

EXAMPLE VIII

Double stranded polydeoxyadenylic acid:polybiotinylated deoxyuridylic acid was synthesized as follows. The double stranded oligonucleotide polydeoxyadenylic acid: polythymidylic acid (20 ug) of length 300 basic pairs, dissolved in 200 ul exonuclease III buffer consisting of Tris-HCl pH 8.0 (70 mM); magnesium chloride (1.0 mM) and dithiothreitol (10 mM) was incubated with 100 units exonuclease III for 20 minutes at 20° C. The partially digested oligonucleotide was immediately extracted with phenol, and the DNA was precipitated with 70% aqueous ethanol. The partially digested oligonucleotide was redissolved in 20 ul 5 mM tris-HCl pH 7.6 and incubated at 20° C. for 2 hours in a reaction containing 2'—deoxy-adenosine-5'-triphosphate (15 uM) thymidine-5'-triphosphate (the amount determines the degree of substitution) and biotinylated 5-(3-amino-1-propene)2'-deoxyuridine-5'-triphosphate (5 uM), Klenow DNA polymerase 1 (200 units) dissolved in 0.1 mM) potassium phosphate, pH 8.0 at a concentration of 0.2 units/ul. The biotinylated poly dA:poly dT, biotinyl dU was purified by gel filtration chromatography on Sephadex G-100. The DNA was enthanol precipitated and redissolved in 20 ul of solution containing sodium acetate pH 4.6 (30 mM), sodium chloride (50 mM), zinc sulfate (1 mM) and glycerol (5%). $S_1$ nuclease (200 units) was added, and the reaction was incubated at 37° for 10 minutes. The reaction was stopped with 1 ml ammonium acetate (4M) and 6 ml ethanol. The DNA was repurified by G-100 gel filtration chromatography and ethanol precipitation.

EXAMPLE IX

Ligation of poly dA:poly dT, biotinyl dU to oligodeoxyribonucleotides was accomplished as follows: DNA fragments from alkali sheared purified DNA (as described in Example VIII) were digested with $S_1$ nuclease and repurified by phenol extraction and ethanol precipitation. Blunt ended DNA fragments (1 ug) and poly dA:poly dT, biotinyl dU (2 ug) were dissolved in 6 ul at a buffer containing tris-HCl pH 7.4 (66 mM), magnesium chloride (6.6 mM), adenosine triphosphate (24 mM) and dithiothreitol (1.0 mM), $T_4$ DNA ligase (50 units) was added, and the volume brought to 20 ul with water. The reaction was incubated 3 hours at 37° C. The DNA was purified by gel filtration chromatography through Sephadex G-1.00 and was ethanol precipitated.

EXAMPLE X

5-Hydroxymethyl-2'-deoxycytidylic acid was prepared by enzymatic hydrolysis of non glycosylated phage $T_4$ DNA. Purified phage DNA (2 mg), dissolved in 1 ml 50 mM tris pH 7.4 and 10 mM magnesium chloride, was incubated 20 hours with deoxyribonuclease I at 37°. The pH was adjusted to 9.0 and sodium chloride (20 mM) added. Snake venom phosphodiesterase (0.05 g units in 0.5 ml water) was added and incubation continued at 37° for 5 hours. An additional 0.05 units phosphodiesterase was added and incubation continued 18 hours. Nucleotides were separated by gel filtration chromatography through Sephadex G-50. 5-hydroxymethyl-2'-deoxycytidylic acid was purified by reverse phase high pressure liquid chromatography.

EXAMPLE XI 5-(4-aminobutylaminomethyl)-2'-deoxyuridylic acid was obtained by enzymatic hydrolysis of DNA from phage øW-14. The phage was grown on *Pseudomonas acidovorans* 29 according to Kropinski and Warren, *Gen. Virol.* 6, 85 (1970), and the phage DNA purified according to Kropinski et al, *Biochem.* 12, 151 (1973). The DNA was enzymatically hydrolyzed with deoxyribonuclease I and snake venom phosphodiesterase using the procedure described elsewhere (Example X). 5-(4-aminobutylaminomethyl)-2'-deoxyuridylic acid was purified by reverse phase high-pressure liquid chromatography.

EXAMPLE XII

Biotinylated-5-(4-aminobutylaminomethyl)-2'-deoxyuridylic acid was prepared as follows: Biotinyl-n-hydroxysuccinimide ester (70 mg 0.2 m mol) dissolved in 1 ml dimethylformamide was added to 5-(4-aminobutylaminomethyl)-2'-deoxyuridylic acid in 20 ml 0.1M sodium borate pH 8.5. After 4 hours the solution was concentrated to 0.5 ml by evaporation, and the biotinylated nucleotide was purified by reverse phase high pressure liquid chromatography.

EXAMPLE XIII 5-formyl-2'-deoxyuridine prepared according to Mertes and Shipchandler, *J. Heterocyclic Chem.* 1, 751 (1970). 5-hydroxymethyluricil (1 mmol) dissolved in 20 ml dimethylsulfonate was heated at 100° C. with manganese dioxide (2.5 mmol) for 15 minutes. The solvent was evaporated at reduced pressure. The residue was taken up in hot ethanol and recrystallized from ethanol to yield 5-formyluracil, 5-formyluracil (0.10 g) was silylated and dissolved in dry acetonitrile (2.5 ml). 2-deoxy-3,5-di-0-p-toluyl-D-ribofuranosyl chloride (Bhat, *Syn. Proc. in Nucleic Acid Chem.*, Vol. 1, p. 521 (1968) (0.22 g) and molecular sieves (0.2 g) were added, and the mixture stirred at 25° C. for 40 hours under anhydrous conditions. The mixture was filtered and evaporated. The resulting oil was treated with anhydrous ethanol (2 ml) and chromatographed on silica gel to obtain the partially pure anomer which was recrystallized from ethanol (M.P. 195°–196° C.) The toluyl groups were removed by reaction of the product in methanol benzene with sodium methoxide. The mixture was neutralized with Dowex 50 ($H^+$). 5-formyl-2'-deoxyuridine was recrystallized from ethanol M.P. 175°–176° C.

EXAMPLE XIV

Biotin was coupled to 5-formyl-2'-deoxyuridine as follows: To 5-formyl-2'-deoxyuridine (0.320 g, 1.0 mmol) dissolved in 300 ml 0.05 M sodium borate, was added biotinyl-1,6-diaminohexane amide (0.74 g, 2 mmol). After stirring one hour, sodium borohydride (0.2 g, 5 mmol) was added and stirring continued for an additional 4 hours followed by the addition of 8 ml 1 M formic acid. The biotinated compound was purified by reverse phage HPLC eluting with methanol: 0.5 M triethyl ammonium acetate, pH 4.0.

EXAMPLE XV

Biotin was coupled to 5-amino-2'-deoxyuridine as follows: 5-amino-2'-deoxyuridine (0.24 g, 1 mmol), biotin (0.25 g, 1 mmol) and dicyclohexylcarbodiimide (0.21 g, 1 mmol) were dissolved in dry dimethyl formamide and stirred at room temperature overnight. After filtration and evaporation of the solvent, the residue was washed with ether. The biotin-coupled product was purified by reverse phase high pressure liquid chromatography using a water methanol gradient.

EXAMPLE XVI 5-(oxy)acetic acid-2'-deoxyuridine was prepared according to a procedure of Deschamps and DeClerq, *J, Med. Chem.*, 21, 228 (1978). 5-hydroxy-2-deoxyuridine (282 mg, 1.15 mmol) was dissolved in 1.16 ml, 1 N potassium hydroxide (1.16 mmol) after which iodoacetic acid (603 mg, 3.4 mmol) in 1 ml water was added. After reaction at room temperature for 48 hours 1N HCl (1.06 ml) was added. Concentration of this solution and addition of ethanol yielded a precipitate which was filtered, washed with cold ethanol and recrystallized from hot ethanol.

EXAMPLE XVII

Biotinyl-1,6-diaminohexane amide was coupled to 5-(oxy)acetic acid-2'-deoxyuridine as follows: Biotinyl-1,5-diaminohexane amide (0.74 g, 0.2 mmol), 5-(oxy)acetic acid-2'-deoxyuridine-(0.60 g, 0.2 mmol) and dicyclohexylcarboimide (0.41 g, 0.2 mmol) were dissolved in 5 ml dry dimethylformamide and remained overnight at room temperature. The reaction was subsequently filtered and the solvent removed by evaporation. The residue was washed with 0.1 N HCl and ether. The biotinated uridine derivative was purified by reverse phase high pressure liquid chromatography using a water-methanol gradient.

EXAMPLE XVIII

Phosphorylation of 5-substituted pyrimidine nucleosides was accomplished by the general procedure described below for biotinated-5-(oxy)acetic acid-2'-deoxyuridine. The nucleoside (0.16 g, 0.5 mmol) was dried by repeated evaporation from dry pyridine and redissolved in 10 ml dry pyridine. Monomethoxytrityl chloride (0.30 g, 0.8 mmol) was added and the mixture stirred at room temperature in the dark for 18 hours. The solution was diluted with chloroform (200 ml) and extracted with 0.1 M sodium bicarbonate. The organic layer was dried and evaporated. The tritylated nucleoside was redissolved in dry pyridine (20 ml) and acetylated by reaction at room temperature with acetic anhydride (0.1 ml, 20 mmol). The mixture was cooled to 4° C. and methanol (40 ml) added. After stirring 10 hours at room temperature, the reaction was concentrated by evaporation. The compound was detritylated by dissolving in 1% benzene sulfonic acid in chloroform (20 ml). After evaporation of solvent the nucleoside was purified by chromatography on silica gel eluting with 2% methanol:chloroform. The 3'-acetylated nucleoside was dried by repeated evaporation of dry pyridine. A mixture of phosphorous oxychloride (100 ul, 1 mmol), (1-H), 1,2,4-triazoic (140 mg, 2.2 mmol) and triethylamine (260 ul, 2.0 mmol) was stirred in 5 ml anhydrous dioxane at 10°–15° C. for 30 minutes and at room temperature for 1 hour. This was added to the 3'-acetylated nucleoside, and the mixture stirred at room temperature for 1 hour after which it was cooled to 0° C. Water (5 ml) was added and the reaction stirred at room temperature for 18 hours. Barium chloride (100 mg, 5 mmol) was added and the barium salt of the nucleotide collected by filtration. The salt was washed with water and ether. The barium salt was converted to the sodium salt by stirring with Dowex 50 ($Na^+$ form) in 10 ml water for 4 hours at room temperature. 2N sodium hydroxide (2N, 10 ml) was added and the reaction stirred for 15 minutes at room temperature after which it was neutralized by addition of excess Dowex 5.0 ($H^+$) form. The deacetylated nucleotide was concentrated by evaporation and purified by reverse phase high-pressure chromatography.

EXAMPLE XIX 5-substituted pyrimidine triphosphates were chemically prepared from their respective 5' monophosphates using a procedure of Michelson, *Biochem Biophys* Acta, 91, 1, (1964). The example of 5-hydroxymethyl-2'-deoxycytidine-5'-triphosphate will be given. The others were similarly prepared. 5-hydroxymethyl-2' deoxycytidylic acid (free acid) (0.63 g, 0.2 mmol) was converted to its tri-n-octylammonium salt by suspending in methanol and addition of tri-n-octylammonium hydroxide (0.74 g, 0.2 mmol). The suspension was refluxed until a clear solution was obtained and the solvent removed under vacuum. The salt was dried by dissolution in and subsequent evaporation from dry pyridine several times. To the salt, dissolved in dry dimethylformamide (0.1 ml) and dioxane (1 ml) was added diphenylphosphochloridate (0.1 ml) and tri-n-butylamine (0.2 ml). After 25 hours at room temperature, solvent was removed and ether was added to precipitate the nucleoside-5'-diphenylpyrophosphate. This was dissolved in dioxane (0.5 ml) and a solution of di(tri-n-butylammonium) pyrophosphate (0.5 mmol) in 1 ml pyridine was added. After 45 minutes at room temperature, the mixture was concentrated under vacuum to a small volume. The crude product was precipitated with ether. This was dissolved in 0.1M phosphate buffer pH 8.0. The trisphosphate was purified by chromatography on DEAE cellulose eluting with a gradient of 0.1 to 0.6 M triethylammonium bicarbonate ph 7.5.

EXAMPLE XX

DNA was labeled with 5-substituted pyrimidine triphosphates by nick translating DNA in the presence of the appropriate triphosphate. An example follows for labeling purified DNA with biotinylated 5-formyl-2'-deoxyuridine. DNA (20 ug/ml) was incubated at 14° C. in the presence of magnesium chloride (5 mM)2'-deoxy-cytidine-5'-triphosphate (15 mM), 2'deoxyadenosine-5'-triphosphate (15 uM), 2'-deoxyguanosine-5'-triphsophate (15 uM), biotinylated-5-formyl-2'-deoxyuridine-5'-triphosphase (20 uM), activated pancreatic deoxyribonuclease I (13 mg/ml), *E. coli* deoxyribonuclease acid, polymerase I (40 units/ml) and tris HCL, pH 7.4 (50 mM). After 2 hours the reaction was stopped by addition of 0.3M EDTA (0.05 ml) followed by heating at 65° for 5 minutes. Labeled oligonucleotide was purified by gel filtration chromatography through Sephadex G-100 and precipitation from cold ethanol.

EXAMPLE XXI

Precipitation of Glucosylated DNA by Concanavalin A

Reaction mixtures (1.0 ml) were prepared in 1.5 ml eppendorf tubes as follows:

| | |
|---|---|
| Sodium potassium phosphate, pH 6.5 | 10 mM |
| NaCl | 150 mM |
| $MgSO_4$ | 5 mM |
| $CaCl_2$ | 1 mM |
| DNA (T4 of calf thymus) | 50 ug |
| Cancanavalin A (10 mg/ml) | 50–500 ug |

Reactions were started by the addition of concanavalin A (Con A). The solutions were mixed and left at room temperature for 60 minutes. The tubes were centrifuged at 1200 g for 15–20 minutes. The supernatants were diluted and the $A_{260}$ was measured.

Since Con A absorbs at 260 nanometers, control solutions lacking DNA but containing Con A were prepared. The Con A absorbance was subtracted from the absorbence obtained in the complete reaction mixtures.

The results of this reaction are presented in accompanying FIG. 1.

EXAMPLE XXII

Binding of Glucosylated DNA to Concanavlin A

Phage T4 DNA and phage DNA were labeled by incorporation of $H^3$-deoxyadenosine triphosphate into the DNA by nick translation according to the Rigby et al procedure. T4 DNA was nick translated to a specific activity of $5 \times 10^5$ cpm/microgram and an average double-standed size of 5 kilobases. Lambda DNA was nick translation to a specific activity of $3 \times 10^5$ cpm/microgram and an average double stranded size of 6.0 kilobases as determined by agarose gel electrophoresis. Unincorporated nucleotides were removed from the reaction mixtures by Bio-Gel P-60 chromatography.

Con A sepharose was prepared as described by the manufacturer (Pharmacia). One ml of settled gel contained 18 mg of bound Con A. One ml columns were prepared in sterile pasteur pippetes and were equilibrated with PBS (0.15 M NaCl; 0.01 M sodium potassium phosphate, pH 6.5).

$H^3$-DNA samples were prepared in 0.5 ml of buffer (as described in Example XXI but without Con A). T4 DNA solutions contained 176,000 cpm/0.5 ml, and DNA solutions contained 108,000 cp./0.5 ml. A 0.5 ml sample was applied to the column.

A 10.5 ml volume of buffer was passed through the column, and the eluate fractions (0.33 m) were collected and counted in a Beckman LSC-100 scintillation counter in a 3.5 ml reafluor cocktail (Beckman). The results (FIGS. 2A and 2B) show that non-glucosylated DNA was not bound whereas glucosylated T4 DNA was bound to the column. The bound T4 DNA was removed by washing the column with a higher pH buffer (Tris-HCl, pH 7.2–8.2).

Figure 3B:
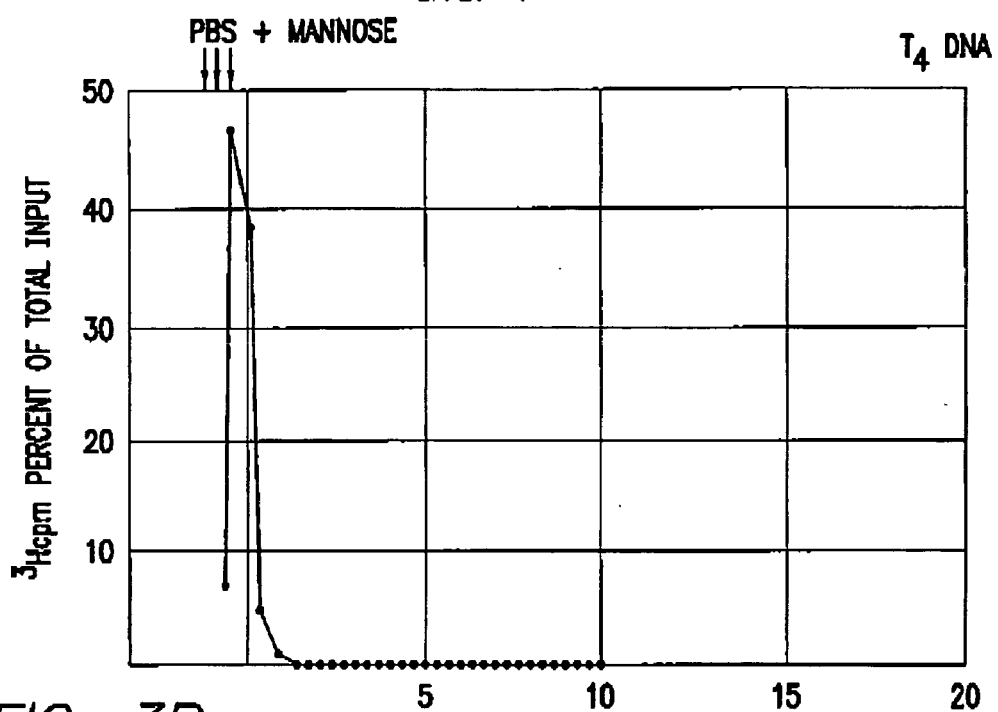
FIG. 3B is a graph that illustrates the recovery (measured as a percent) of tritium-labeled T4 DNA using a Con A-sepharose column when mannose is included in the buffer, as described in Example XXII.
Figure 3B:
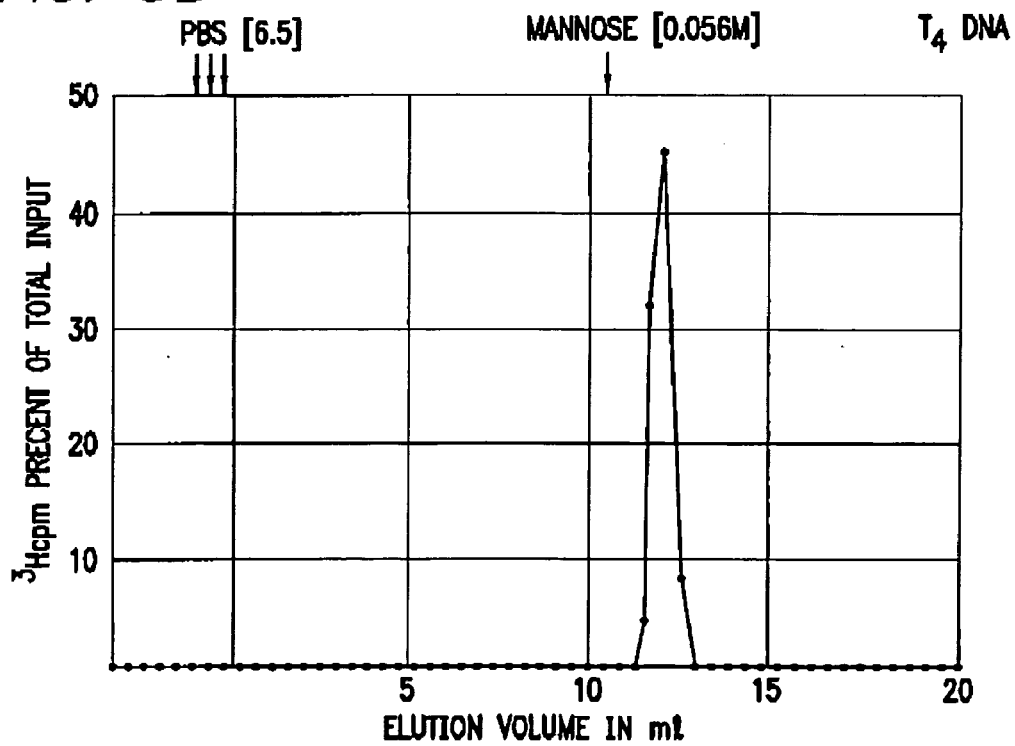

Furthermore, consistent with the interaction of glucose and Con A, mannose, when included in the buffer in which the DNA is applied to the column, prevents binding of glucosylated DNA to Con A sepharose. Also, mannose-containing buffer (PBS-containing 0.056 M mannose) removes bound T4 DNA from Con A sepharose (FIGS. 3A and 3B).

Further illustrative of the practices of this invention directed to nonradioactive methods or techniques of assaying for specific nucleic acids, the following example deals with the use of the sugar-lectin system. This example deals with the use of DNA which is not glycosylated in nature but rather has had a maltotriose group added thereto by way of nick translation described herein. The maltotriose modified dUTP and DNA modified therewith bind specifically to a column of concanvalin A covalently bound to sepharose. By this technique and in accordance with the practices of this invention, there is provided a means for specifically labeling any nucleic acid with sugars. As previously indicated herein, nick translation is only one of a number of techniques and approaches possible for the production of the modified nucleic acids in accordance with this invention.

EXAMPLE XXIII

Lambda DNA was nick translated as described herein with maltotriose coupled to 5-(3-amino-1-propenyl)-2'-deoxyuridine-5'triphosphate and $^3$H-2'-deoxyadenosine-5'-triphosphate. Under these conditions DNA was substituted to 40 percent of its thymidine residues with the maltotriose nucleotide and had a specific activity of $8 \times 10^5$ counts per minute (cpm) per microgram of DNA. A control sample of DNA substituted only with $^3$H-dATP had a specific activity of $6 \times 10^5$ cpm per microgram DNA. The nick translated DNA samples were purified free of reaction mixture components by Biogel P-60 chromatography as described herein.

Figure 2A:
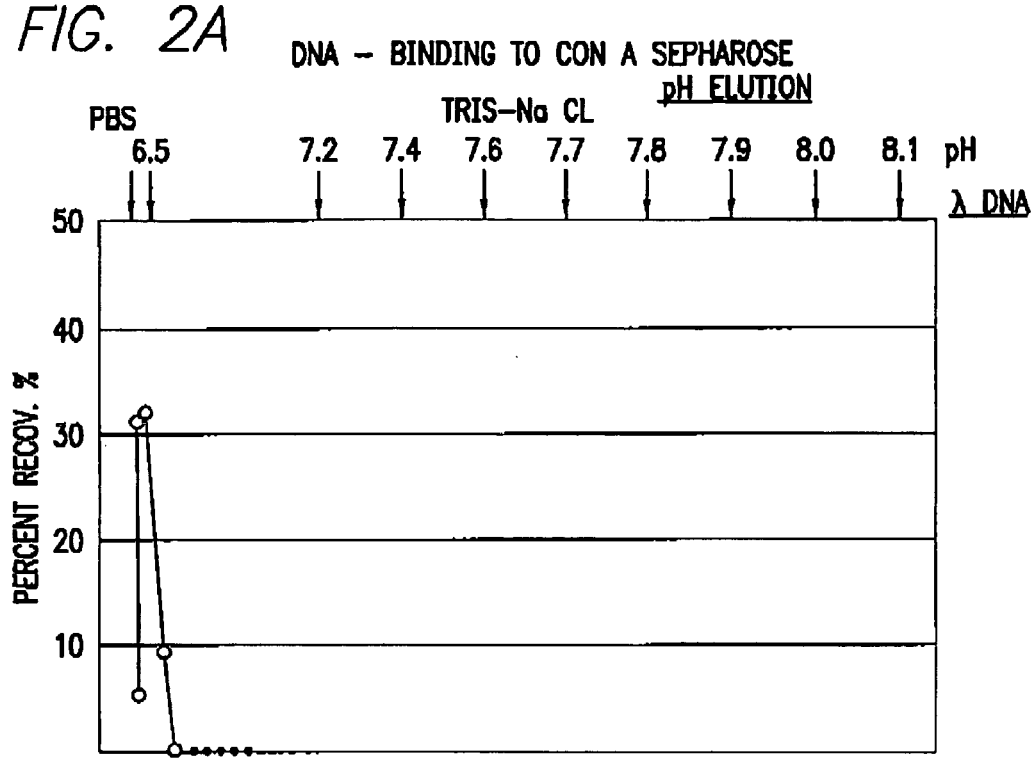
FIG. 2A is a graph that shows the recovery (measured as a percent) of tritium-labeled lambda DNA using a Con A-sepharose column as described in Example XXII. Non-glucosylated DNA was not bound whereas glucosylated DNA was bound to the column.
Figure 2B:
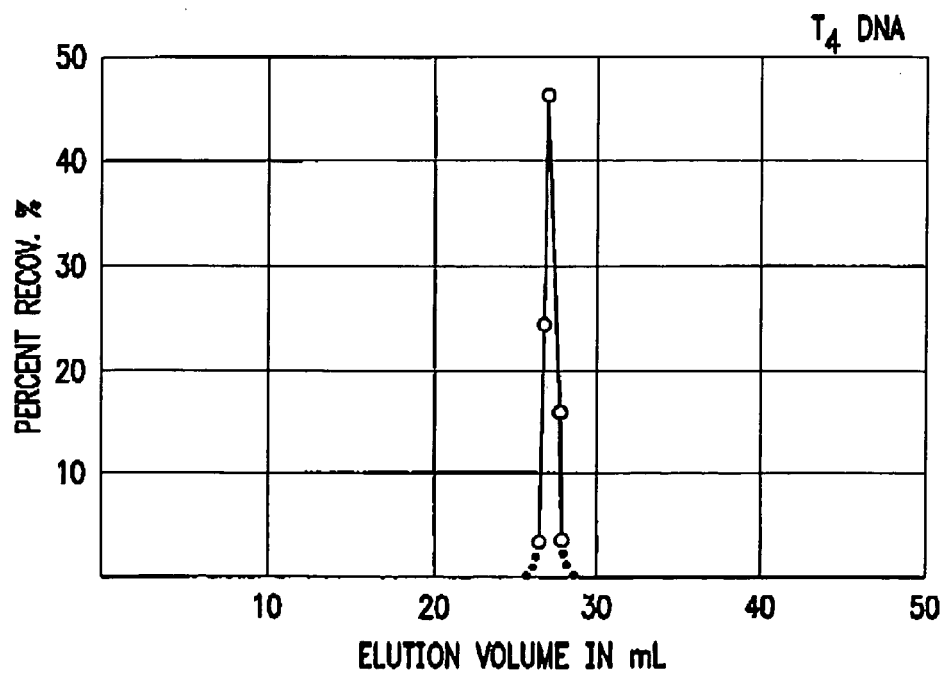
FIG. 2B is a graph that shows the recovery (measured as a percent) of tritium-labeled T4 DNA using a Con A-sepharose column as described in Example XXII. Non-glucosylated DNA was not bound whereas glucosylated DNA was column bound.
Figure 4A:
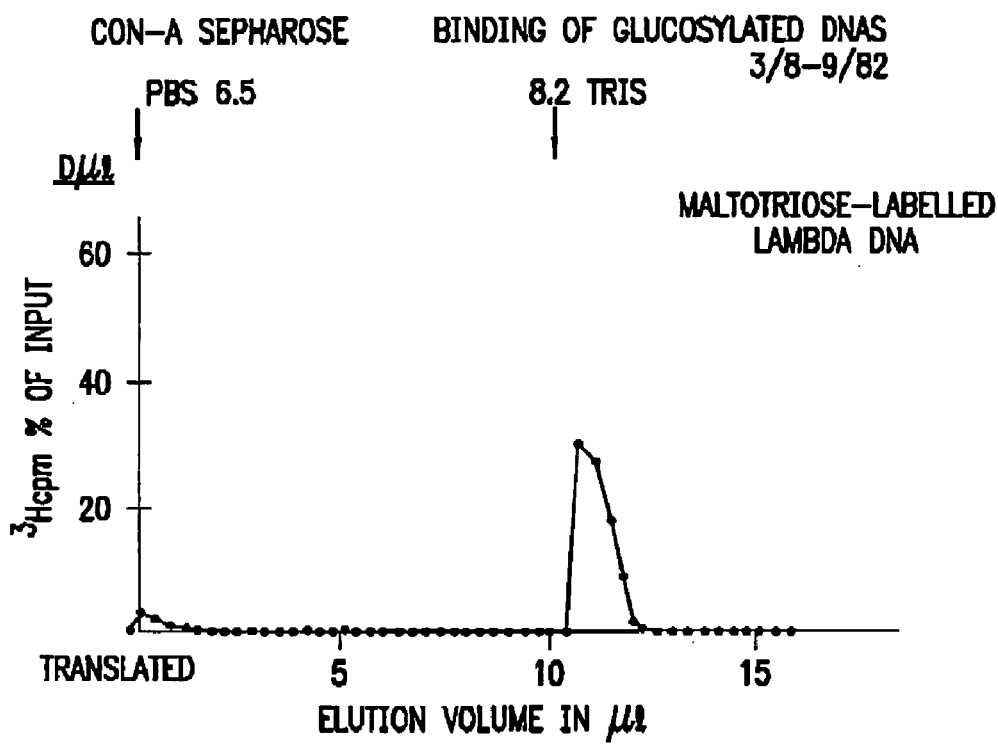
FIG. 4A is a graph that shows the retention of maltotriose labeled lambda DNA using a Con A-sepharose column as described in Example XXIII.
Figure 4B:
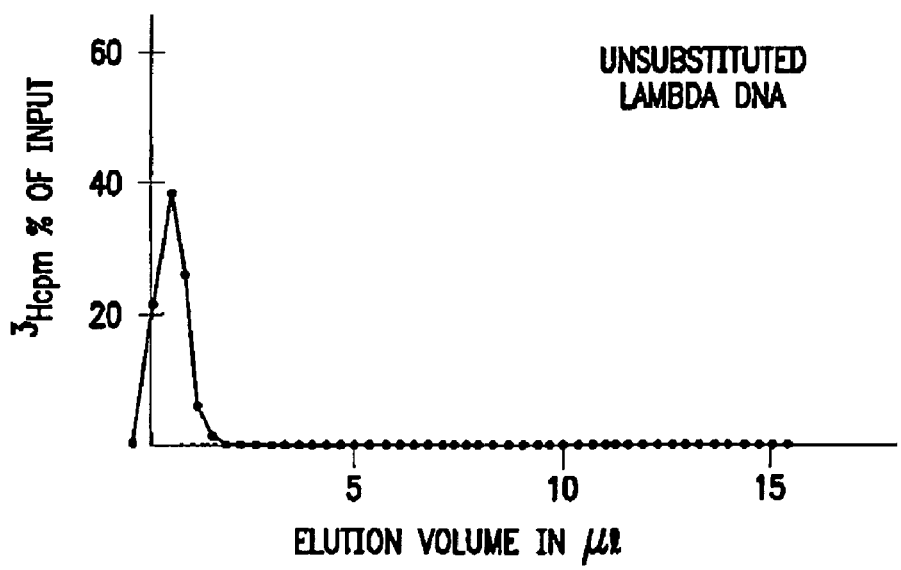
FIG. 4B is also a graph that shows the retention of unsubstituted tritiated lambda DNA using a Con A-sepharose column as described in Example XXIII.

The purified samples were applied to Con A-sepharose columns as described in FIGS. 2A and 2B. The maltotriose-labeled DNA was retained on the column when washed with PBS but was removed by subsequent elution with 10 mM Tris-HCl, pH 8.2 (FIG. 4A). The unsubstituted tritiated DNA did not bind to the column at pH 7.4 (FIG. 4B).

EXAMPLE XXIV

Potentially immunogenic heptenes may be introduced at the 5 position of uridine by a variety of methods in the literature. 5-(perfluorobutyl)-2'-deoxyuridine was synthesized using a method of Cech et al, *Nucl. Acids Res.* 2, 2183 (1979). Copper-bronze was prepared by reacting copper sulfite (5 g, 20 mmol) with zinc powder (2 g) in 20 ml water. The mixture was decanted, and the residue washed with water and then 5% hydrochloric acid and water. Just before use, the solid (2 g) was activated with 2% iodine in acetone (20 ml). After filtration the residue was washed with acetone:concentrated hydrochloric acid and then pure acetone. Activated copper-bronze (130 mg, 2 mmol) and 1-iodo-1'2,2',3,3',4,4'heptafluorobutane (1.3 mg, 4 mmol) were stirred in 3 ml dimethylsulfoxide at 110° C. for 1 hour. After cooling and filtration, 2'-deoxyuridine (245 mg, 1 mmol) was added, and the mixture heated at 110° C. for 1 hour. Water (5 ml) was added, and the mixture extracted with ether. The ether extracts were dried and evaporated under reduced pressure. The residue was chromatographed on a silica gel column eluting with ethylacetate.

EXAMPLE XXV

Tubericydin was substituted at the 5 position by derivitizing the 5-cyano compound, toyocamycin. An example is the synthesis of 4-amino-5 (tetrazol)-5-yl)-7-(B-D-ribofuranosyl) pyrrolo[2,3-d]pyrimidine using a procedure of Schram and Townsend, *J. Carbohydrate*, Nucleosides: Nucleotides 1, 38 (1974). Toyocamycin (1.0 g) dissolved in water (100 ml) and glacial acetic acid (13 ml) was heated to reflux. Sodium azide (7.5 g) was added in 1.25 g portions over 10 hours. The solution was cooled to 5° C. and the precipitated product collected, M.P. 276°–277° C.

EXAMPLE XXVI

5-Cyano-2'-deoxyuridine was prepared according to Bleckley et al, *Nucl. Acids Res.* 2, 683 (1975). 5-Iodo-2'-deoxyuridine (1.0 g, 2.82 mmol) was dissolved in refluxing hexamethyldisilizane (HMDS) (10 ml). Excess HMDS was removed at reduced pressure, and the resulting oil was dissolved in dry pyridine (50 ml). Cuprous cyanide (350 mg, 3.8 mmol) was added, and the solution heated at 160° C. for 20 hours. Pyridine was removed at reduced pressure, and the residue extracted into toluene which was subsequently evaporated. The residue was heated in 50% aqueous ethanol at 100° for 2 hours. The product was purified by reverse-phase high pressure liquid chromatography and recrystallized from ethanol, M.P. 161° C.

EXAMPLE XXVII 4-amino-5-amino methylene-7-(β-D-2-deoxyfuranosyl) pyrrolo[2,3-d]pyrimidine dihydrochloride was obtained as follows. 4-amino-5-cyano-7-(β-D-2-deoxyfuranosyl) pyrrolo[2,3-d]pyrimidine (Toyocamycin) (0.2 g) was dissolved in hydrochloric acid (10 ml). 10% palladium on charcoal (0.1 g) was added as the mixture hydrogenated at 40 psi for 5 hours at room temperature. After filtration the water was evaporated at reduced pressure. The residue was triturated with ethanol, and the product recrystallized from 50% ethanol.

EXAMPLE XXVIII 5-amino-2'-deoxyuridine was prepared from 5-bromo-2'-deoxyuridine according to the procedure of Roberts and Visser, *J. Am. Chem. Soc.* 14:665–669 (1952). 5-bromo-2'-deoxyuridine (2 g, 6.2 mmol) dissolved in liquid ammonia (20 ml) was scaled in a glass tube and heated at 50° for 5 days. The tube was opened, and the ammonia was evaporated. 5-amino-2'-deoxyuridine was recrystallized from 5 ml water and 75 ml hot isopropyl alcohol.

EXAMPLE XXIX 5-(methylamino)-2'-deoxyuridine (0.2 g) was prepared as follows. 5-cyano-2'-deoxyuridine (0.2 g, 0.05 mol) was dissolved in 1 N hydrochloric acid (10 ml). 10% palladium on charcoal (0.1 g) was added, and the mixture hydrogenated at 40 p.s.i. for 10 hours at room temperature. The mixture was filtered and the water evaporated at reduced pressure. The residue was triturated with ether, and the product was recrystallized from 80% ethanol.

EXAMPLE XXX

Maltose triose was oxidized to the corresponding carboxylic acid by the following method. Maltose triose (0.5 g, 0.94 mmol) was dissolved in water (5 ml). Lead carbonate (0.42 g, 1.1 mmol) and bromine (0.17 ml), 3.3 mmol) were added, and the mixture was allowed to react at room temperature for six days after which no reducing sugar remained. The mixture was filtered, and silver carbonate (0.2 g) added. After refiltering, the filtrate was deionized by elution through Dowex 50 ($H^+$ form). Evaporation of water and drying in the presence of phosphorus pentoxide yielded the desired product.

EXAMPLE XXXI

Maltose triose was coupled to 5-(3-amino-1-propenyl)-2'-deoxyuridine-5' triphosphate by the following procedure. Oxidized maltose triose (190 mg, 0.18 mmol) was dissolved in dimethylformamide (0.8 ml) and cooled to 4° C. Isobutyl chloroformate (25 mg, 0.18 mmol) and tri-n-butylamine (43 ul, 0.38 mmol) were added, and the solution allowed to react at 4° C. for 15 minutes. 5-(3-amino-1-propenyl)-2'-deoxyuridine-5'-triphosphate (9.0 mmol), dissolved in dimethyl formamide (1.2 ml) and 0.1M sodium borate and cooled to 4° C., was added to the above solution. The mixture was incubated at 4° C. for 1 hour and at room temperature for 18 hours. It was then loaded on a DEAE-cellulose column and eluted with a gradient of 0.1 to 0.6 M triethylammonium bicarbonate, pH 7.5. The product was finally purified by reverse phase high pressure liquid chromatography.

Following are Examples XXXII and XXXIII. Example XXXII is a method of tagging allylamine modified dUTP with a fluorescein substituent. This is an example of creation of a self detecting nucleic acid probe. Example XXXIII is a method of labeling preformed double helical nucleic acids at the $N^2$ position of guanine and the $N^6$ position of adenine. Example XXXVII has the detector molecule linked to the probe. Chromosoma 84: 1–18 (1982) and Exp. Cell Res. 128:485–490, disclose end labeling of RNA with rhodamine. However, the procedure of this invention is less disruptive and labels internal nucleotides.

EXAMPLE XXXII

Fluorescein was coupled to 5-(3-amino-1-propyl)-2'-deoxyuridine-5'-triphosphate (AA-dUTP) as follows. AA-dUTP (10 mmol), dissolved in 2 ml sodium borate buffer (0.1 m), pH 9.0, was added to fluorescein isothiocyanate (10 mg, 25 mmol) dissolved in 1 ml dimethylformamide. After four hours at room temperature the mixture was loaded onto a DEAE-cellulose column equilibrated in triethylammonium bicarbonate buffer, pH 7.5. The fluorescein coupled AA-dUTP was purified by elution with a gradient of from 0.1 to 0.6 m triethylammonium bicarbonate, pH 7.5.

EXAMPLE XXXIII

DNA may be modified by reaction with chemical alkylating agents. Lambda DNA was alkylated in $N^2$ position of guanine and $N^6$ position of adenine by reacting DNA with aromatic hydrocarbon 7-bromomethylbenz[a]anthracene. 7-bromomethylbenz[a]anthracene was obtained as follows. 7-methyl[a]anthracene in carbon disulfide solution was cooled in a freezing mixture and treated dropwise with a molar equivalent of bromine. After 30 minutes, the product in suspension was collected, and was washed with dry ether and recrystallized from benzene. The yield was 66% with melting point 190.5°–191.5° C.

DNA, purified from phage Lambda, (1.6 mg) was solubilized in 5.0 ml of 20 mM potassium phosphate pH 6.5. To 4.0 ml of DNA solution was added 500 micrograms 7-bromomethylbenz[a]anthracene in dry acetone. After 30 minutes at 20°, the DNA was precipitated with two volumes of cold ethanol. The precipitate was washed successively with ethanol, acetone and ether to remove any unbound 7-bromomethylbenz[a]anthracene. Enzymatic hydrolysis of the DNA to nucleosides and subsequent chromatography of the products on Sephadex LH-20 columns, indicated that 18% of the adenine and 48% of the guanine in DNA were modified in $N^6$ and $N^2$ positions, respectively.

The modified DNA was made single stranded either by (1) heating to 100° for 5 minutes and rapid cooling or (2) incubating with equal volume of 0.1 M NaOH for 10 minutes and then dialyzing the solution for four hours against 1 ml tris-HCl pH 8.0 containing 0.5 ml EDTA to keep the DNA in single-stranded form.

EXAMPLE XXXIV

A DNA probe was ligated to a synthetic DNA composed of repeated sequences of *E. coli* lac operator DNA. After hybridization to detect antiprobe sequences, the hybridized DNA was detected by reaction with biotinylated lac repressor which was, in turn, detected by an enzyme linked immuno sorbent assay using goat antibiotin IGG to react with the biotin and a second antibody coupled to horse radish peroxidase. The lac polyoperator DNA has been described by Caruthers (Second Annual Congress for Recombinant DNA Research, Los Angeles, 1982), and it was ligated, in a blunt end ligation, using T4 ligase, to an adenovirus DNA probe. In situ hybridization of the polyoperator-labeled probe DNA was carried out as described by Gerhard et al (*Proc. Natl. Acad. Sci.* USA, 78, 3755 (1981). Biotinylated lac repressor was prepared as described by Manning et al (Chromosoma, 53, 107–117 (1075) and was applied to adenovirus infected cells, fixed to a glass slide, in Binding buffer composed of (0.01 MK Cl, 0.01 M tris (pH 7.6), 0.01 M $MgSO_4$, 10 MEDTA, $10^{-4}$ M DTT, 5% DMSO (dimethyl sulfoxide) and 50 µg/ml bovine serum albumin by J. Miller, *Experiments in Molecular Genetics*, Cold Spring Harbor Laboratory (1972). The slides were washed in binding buffer to remove unbound biotinylated lac repressor and then assayed for biotin using the horse radish peroxidase-linked double antibody procedure. This procedure could be adapted to create an affinity column where the probe could be bound to immobilized repressor protein and then removed by elution with a specific inducer, for example, isopropylthigalactoside or thiomethylgalactoside. The affinity of the repressor-operator complex is quite high $10^{-11}$ M. When a specific inducer binds to the repressor the operator-repressor complex collapses.

EXAMPLE XXXV

5-Bromo-2'-deoxyuridine-5'-phosphate was prepared as follows: 2'-Deoxyuridine-5'-phosphate (6.2 g) was suspended in a mixture of 60 ml pyridine and 30 ml acetic acid. Bromine (0.84 ml) was added with stirring in an ice water bath and stirring continued for 20 hours at room temperature. The solution was concentrated by vacuum. After redissolution in a minimum of water a crude product was precipitated by addition of ethanol. The crude product was chromatographed on Dowex 50 ($H^+$) and eluted with water.

The free acid product was precipitated from the concentrated eluent by addition of ethanol.

EXAMPLE XXXVI

Calf intestine alkaline phosphate was biotinylated as follows: The enzyme (1 mg, 7.7 mmol) was chromatographed on a G-50 column eluting with 0.1 M Hepes buffer pH 8.0 containing 0.1 M sodium chloride. The pooled fractions were reacted with N-biotinyl-6-amino-caproic acid-N-hydroxysuccinimide ester (0.675 mg, 0.77 mmol) dissolved in 10 ml dimethylformamide at room temperature for 1 hour. Sodium periodate (0.1 M 125 ul) was added and stirring continued for 2 hours. The mixture as dialyzed at 4° overnight in 0.1 M Hepes buffer pH 8.0 with 0.1 M NaCl after which the pH was adjusted to 7.4. Biotin hydrazide (0.1 M, 0.5 ml) dissolved in 0.1 M Hepes buffer pH 7.4 and 0.1 M NaCl was added and the reaction stirred for 30 minutes at room temperature. The pH was adjusted to 8.0 with 0.2 M sodium carbonate and 0.5 ml of freshly prepared 0.1 M sodium borohydride in water was added, the solution was dialyzed against 0.1 M tris buffer pH 8.0 with 0.1 M NaCl.

EXAMPLE XXXVII

6-Cyano-2'-deoxyuridine-5'-phosphate was prepared similarly to a procedure of Veder et al, *J. Carbohydr. Nucleosides, Nucleotides*, 5, 261 (1978). 5-bromo-2'-deoxyuridine-5'-phosphoric acid (2.0 g, 15 mmol) dried by successive evaporation from pyridine was dissolved in 50 ml dimethylsulfide. Sodium cyanide (490 mg, 10 mmol) was added and the solution stirred at room temperature for 2 days. The solution was diluted with 400 ml water and the pH adjusted to 7.5. It was applied to a DEAE-cellulose column ($HCO_3^-$ form) washed with 2000 ml 0.02 M triethylammonium bicarbonate to yield the desired product.

EXAMPLE XXXVIII 6-(Methylamino)-2'-deoxyuridine-5'-phosphoric acid was prepared as follows: 6-Cyano-2'-deoxyuridine-5'-phosphoric acid (0.2 g, 60 mmol) was dissolved in 0.1 M hydrochloric acid. After addition of 10% palladium on charcoal (0.1 g), the mixture was hydrogenated at 40 psi for 20 hours at room temperature. The mixture was filtered, neutralized with lithium hydroxide and lyophilized. The product residue was extracted with ethanol.

EXAMPLE XXXIX

Horse radish peroxidase (20 mg) dissolved in 5 ml distilled water was added to 1.0 ml freshly prepared 0.1 M sodium periodate solution. After stirring at room temperature for 20 minutes it was dialyzed overnight at 4° C. against 1 mM sodium acetate pH 4.4. Biotin hydrazide (2.6 mg, $5 \times 10^{-2}$ mmol) dissolved 2.0, 0.1 M Hepes buffer pH 7.4 with 0.1 M sodium chloride was brought to pH 0.0 with 0.2 M sodium carbonate and 0.5 ml of a freshly prepared 0.1 M sodium borohydride solution in water was added. After 2 hours at 4° C. the protein was purified on a Sephadex G-50 column eluting with 0.1 M Hepes and 0.1 M NaCl.

EXAMPLE XL

Carrot acid phosphatase has been mentioned by Brunngraber and Chargaff, *J. Biol. Chem.*, (1967) 242, 4834–4840 as a byproduct of the purification of phosphotransferase and has been purified to a specific activity of 460 uM/mg/min at 37° C. with paranitrophenylphosphate as the substrate. The purification involved the steps of (a) absorption of non-specific proteins by DEAE cellulose; (b) acid purification of the enzyme; (c) acetone fractionation; (d) concanvalin A affinity chromatography; (e) hydroxyapatite chromatography and (f) Sephadex G-100 fractionation. The specific activity of the enzyme subjected to the Sephadex G-100 fractionation due to loss of activity in the preceding affinity chromatography step (d) was 170 uM/mg/m. By changing elution conditions at step (d), these losses can be avoided with the result that the specific activity of the enzyme before the Sephadex G-100 fractionation can be improved to 340 uM/mg/m. The Sephadex G-100 fractionation step should yield an enzyme having a specific activity of 800 uM/mg/m or higher. Carrot acid phosphatase was biotinylated using a procedure of Wilchek et al *Biochemistry* 6, 247 (1967). To the enzyme (20 mg) dissolved 0.1 M NaCl, pH 5, was added biotin hydrazide (2.0 mg, $7 \times 10^{-3}$ mmol) and 1-ethyl-3-(3-dimethylaminopropyl) carbodimide hydrochloride (1 mg, $7 \times 10^{-3}$ mmol) dissolved in 0.1M NaCl, pH 5. After 2 hours at 4° C. the enzyme was chromatographed on Sephadex G-50 eluting with 0.1 M sodium acetate, pH 5.0. Of special importance and significance in the practices of this invention is the utilization of self-signaling or self-indicating or self-detecting nucleic acids, particularly such nucleic acids which are capable of being incorporated in double-stranded DNA and the like. Such self-signaling or self-detecting nucleic acids can be created by covalently attaching to an allylamine substituent making up a modified nucleotide in accordance with this invention a molecule which will chelate specific ions, e.g. heavy metals, rare earths, etc. In general, the chelated ion can be detected either (a) by radioactive emission or (b) by using the ion to catalyze a chromogenic or fluorogenic reaction.

By way of example, a solution of 3,4-dinitro phenol is reduced to 3,4-diamino cyclohexane

1)

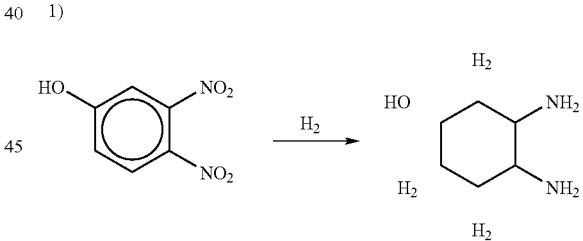

This material is then brominated

2)

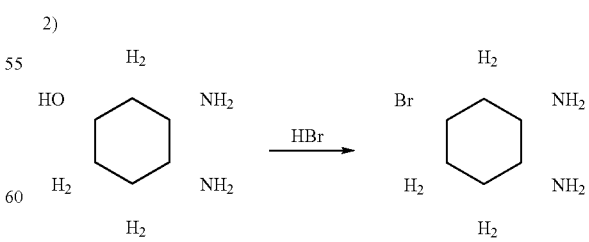

to form 3,4-diamino bromo cyclohexane (dABCH). This compound is reacted with halide (Cl, Br, I) substituted carboxymethyl compound to produce a tetra carboxymethyl derivative or dABCH (TCM-dABCH):

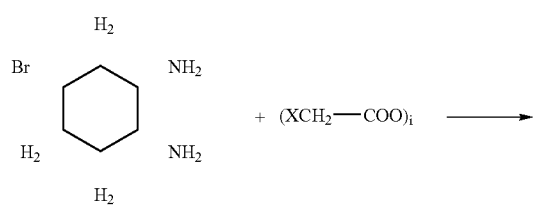

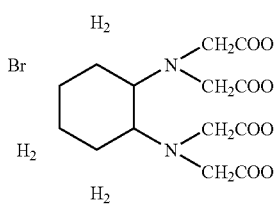

The bromine is substituted by an amino group using soluble ammonia:

4)

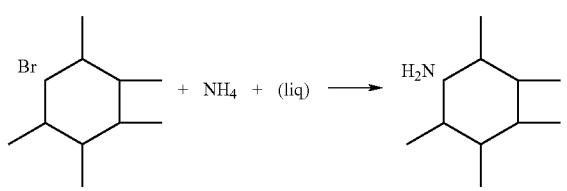

Then this compound is reacted with chloro thiophosgene to produce the isothiocyanate derivative of (TCM-dANCH).

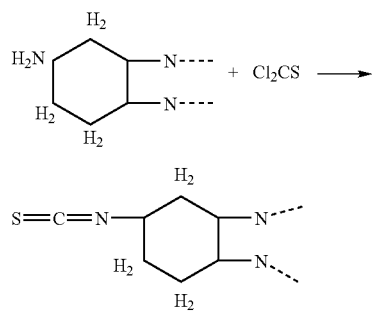

Finally, this compound is reacted with dUTP-allylamine derivative to produce modified

6)

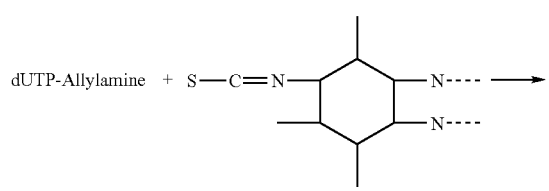

dUTP.

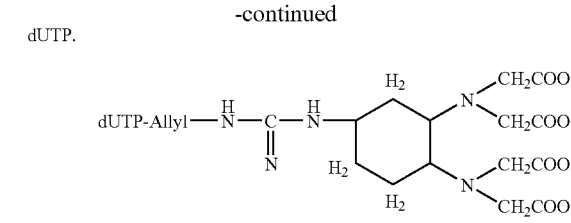

Cobalt or other heavy metal ions or other rare earth ions can be chelated to the compound after step 3 above. Or the nucleic acid can be substituted with this adduct and then the ion added. (Example, cobalt is added at pH 6 where the binding constant is $10^{19}$ M).

Cobalt can be assayed by radioactivity. It can also be detected by its ability to oxidize methylene blue to the leuco form in the presence of molecular oxygen. It can be used to oxidze soluble sulfhydro groups to disulfide bonds again in the presence of molecular oxygen.

This type of self-signaling molecule can be used to monitor any nucleic acid hybridization reaction. It is particularly important for detecting nucleic acids in gels (for example, sequencing gels).

With respect to its use in radioactivity, it can be used to tailor the isotope needed, i.e. if a weak or strong β or γ emitter is needed, that isotope can be chelated. Examples of isotopes that can be used are listed immediately hereinafter.

Antimony-124
Antimony-125
Arsenic-74
Barium-133
Barium-140
Beryllium-7
Bismuth-206
Bismuth-207
Cadmium-109
Cadmium-115m
Calcium-45
Carbon-14
Cerium-139
Cerium-141
Cerium-144
Cesium-134
Cesium-137
Chlorine-36
Chromium-51
Cobalt-56
Cobalt-57
Cobalt-58
Cobalt-60
Erbium-169
Europium-152
Godolinium-153
Gold-195
Gold-199
Hafnium-175
Hafnium-175 + 181
Hafnium-181
Hydrogen-3 see Tritium
Iodine-125
Iodine-131
Iodine-132
Iridium-192
Iron-55
Iron-59
Krypton-85
Lead-210
Lutetium-177
Manganese-54

-continued

Mercury-197
Mercury-203
Molybdenum-99
Neodymium-147
Neptunium-237
Nickel-63
Niobium-95
Osmium-185 + 191
Palladium-103
Platinum-195m
Praseodymium-143
Promethium-147
Protactinium-233
Radium-236
Rhenium-186
Rubidium-86
Ruthenium-103
Ruthenium-106
Scandium-44
Scandium-46
Selenium-75
Silver-110m
Silver-111
Sodium-22
Strontium-85
Strontium-89
Strontium-90
Sulphur-35
Tantalum-182
Technetium-99
Tellurium-125m
Tellurium-132
Terbium-160
Thallium-204
Thorium-228
Thorium-232
Thulium-170
Tin-113
Titanium-44
Tritium
Tungsten-185
Vanadium-48
Vanadium-49
Ytterbium-169
Yttrium-88
Yttrium-90
Yttrium-91
Zinc-65
Zirconium-95

Streptavidin, a protein produced by a *Streptomyces avidinii* is a large molecular weight component of a synergistic pair of compounds which are both present in the culture filtrates of this microorganism. Each of the pair is inactive but in combination are active against gram-negative microorganisms. It has been found that the small component of this antibiotic prevents de novo synthesis of the vitamin biotin and thus, at least in synthetic media, show antimicrobial activity. In complex medium, however, the large component has to be included to exert the same effect on bacteria. This has been shown to be due to the presence of external biotin in the complex medium. The large molecular component has been found to bind external biotin and thus demonstrating the same kind of action as avidin from eggs and oviduct tissues of laying birds.

Streptavidin has been purified and shown to be a 60,000 dalton polypeptide. Like avidin, streptavidin contains four subunits and binds tightly four molecules of biotin. Unlike avidin, however, it is non-glycosylated and it has PI of 5.0 as compared to avidin with PI=10.5. Due to the difference in pI streptavidin does not have a tendency to non-specifically interact with DNA.

Preparation of Streptavidin

A semi-synthetic medium containing salt, 1% glucose, 0.1% asparagine, 0.05% yeast extract and trace elements was prepared. The cultures were grown at 26° C. for three days. Mycellium was removed by centrifugation and protein in the supernatant were absorbed to DEAE-cellulose in a batchwise process after pH was adjusted with 1 M HCl to 7.2. DEAE-cellulose was filtered off and washed with 20 mM Tris-HCl (pH 7.2) until no absorbancy at 280 nm was recorded. Streptavidin was eluted with 20 mM Tris-HCl (pH 7.2) containing-0.5 M NaCl. Ammonium sulfate precipitation was used to further concentrate the streptavidin (50% w/v at 4° C.).

The precipitate was dissolved in water and dialyzed against 1.0 M NaCl, 50 mM $Na_2CO_3$. In the next step affinity column chromatography on iminobiotin sepharose was used. Eluted streptavidin from iminobiotin sepharose column was shown to be chromatographically pure by non-denaturing agarose-gel electrophoresis.

The final purification of streptavidin is accomplished by affinity purification through an iminobiotin-sepharose column. Iminobiotin is an analog of biotin in which the carbonyl of the urea moiety is substituted with an imine function. Iminobiotin will bind avidin and streptavidin at basic pH but the complex is dissociable at acidic pH.

Iminobiotin is prepared from biotin in several steps. Biotin is hydrolyzed by barium hydroxide to cis-3,4-diamino-2-tetrahydrothiophene-valeric acid which is reacted with cyanogen bromide to iminobiotin. The iminobiotin is coupled to amino sepharose via the N-hydroxysuccinimide ester of its hydrobromide salt.

The crude protein mixture from DEAE eluted *Streptomyces avidinii* incubation media is dissolved in 50 mM sodium carbonate and 1.0 M sodium chloride (pH 11) and applied to an iminobiotin column pre-equilibrated with this solution. The column is eluted at pH 11.

Streptavidin is subsequently eluted with 50 mM ammonium acetate, pH 4.0 containing 0.5 M sodium chloride. The eluent is dialyzed three times against 1 mM Tris pH 7.4 and lyophilized to dryness.

In the practices of this invention avidin is useful as a detecting mechanism for labeled DNA, such as biotin-labeled DNA. However, avidin itself, such at about neutral pH, complexes with DNA with the result that any signal derivable from a complex between biotin-labeled DNA and avidin might be lost or be non-detectable in the background due to the complex formation between avidin and unlabeled DNA. This disadvantage of the use of avidin in the practices of this invention is not possessed by streptavidin which does not form a complex with DNA at about neutral pH but is capable of forming a complex with the biotin portion of biotin-labeled DNA.

In another aspect directed to the broad utility of avidin and streptavidin for detecting labeled compounds other than DNA, avidin and streptavidin are particularly effective as detecting mechanisms for labeled proteins, polysaccharides and lipids. By way of example, one can fix to a solid matrix a specific antigen and bind to this antigen an antibody directed against this antigen which itself has been biotinylated. Then one can assay for the presence of this biotinylated antibody by reacting it with avidin or streptavidin complexed with an enzyme, such as calf intestine alkaline phosphatase, or to which fluorescing molecule, as for example fluoroscein has been linked.

The use of the antigen-antibody system for detecting either antigen or antibody is well known. A comparable system is a system based on a glycosylated substrate or molecule and matching or appropriate lectin. In this system the lectin would carry a label, such as fluorescein or appropriate enzyme. In this glycosyl-lectin system the labeled lectin forms a complex with the glycosyl moiety, comparable to the antigen-antibody complex, and this complex comprising the glycosylated molecule and appropriate labeled lectin having the necessary glycosyl or sugar moiety specificity would then present itself eliciting the expected response from the label portion of the labeled lectin making up the glycosyl-lectin complex.

Another aspect of the practives of this invention which is particularly advantageous is to carry out the detection or hybridization in the liquid phase between the DNA sought to be detected and the DNA detecting probe. In this liquid phase system both the DNA molecule to be detected and the appropriate DNA detecting probe are not attached to any insoluble substrate or any insoluble chemical moiety. The advantages of the liquid phase detection system reside in the speed of hybridization or hybrid formation between the DNA to be detected and the appropriate DNA probe therefor. For example, in a solid-liquid system the time required to effect recognition and hybridization formation is about ten times greater than if it were carried out in a completely liquid system, i.e. both DNA to be detected and the detecting DNA are not attached to an insoluble moiety.

The probes prepared in accordance with the practices of this invention are adaptable for use in the detection of viruses and bacteria in fluids as indicated hereinabove. Where the fluids to be examined do not contain large amounts of protein, the viruses therein can be concentrated by absorption on hydroxyapatite and eluted in a small amount of phosphate buffer. When the fluid to be examined contains large-amounts of protein, the viruses can be concentrated by high speed centrifugation.

If antibody were available, absorption on an affinity column and elution with acid would be preferable because it would be possible to process many probes in accordance with the practices of this invention at the same time. The bacteria to be examined is usually readily concentrated by cen In accordance with the practices of this invention, the identification or characerization of the isolated particles, viruses and bacteria, would be hybridization of the characterizing or identifying DNA thereof with a specific single stranded DNA probe prepared in accordance with the practices of this invention. After hybridization, excess non-hybridized probe DNA would be digested with S$_1$ nuclease and exonclease I from $E.\ coli$ at high salt content to suppress the nicking activity of the S$_1$ nuclease, see Vogt, $Methods\ in\ Enzymology$, Vol. 65, pages 248–255 (1980). This nuclease treatment would produce mononucleotides from the excess, non-hybridized single-stranded DNA probe but would leave the double-stranded, hybridized DNA intact. This would then be absorbed at high salt content on Dowex anion exchanger (the nucleotides and the small amount of oligo-nucleotides will not bind to the resin in high salt concentration). The resulting hybridized DNA would then be identified or characterized by various procedures applicable to the practices of this invention.

The special nucleotides of this invention include a phosphoric acid P moiety (also designated hereinbelow as "PM"), a sugar or monosaccharide S moiety (also designated hereinbelow as "SM"), a base B moiety (also designated hereinbelow as "BASE"), a purine or a pyrimidine and a signalling chemical moiety Sig covalently attached thereto, either to the P, S or B moiety (referred to hereinbelow as "PM," "SM" and "BASE," respectively). Following are structural formulas of various base B moieties (BASE) and nucleotides which are modified in accordance with the practices of this invention.

The major purines

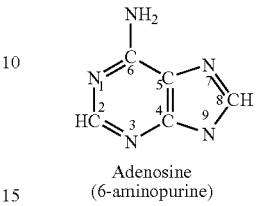
Adenosine
(6-aminopurine)

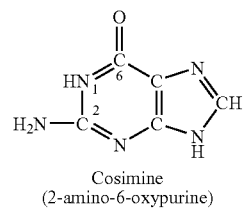
Cosimine
(2-amino-6-oxypurine)

Two minor purines

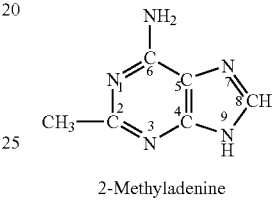
2-Methyladenine

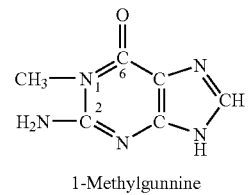
1-Methylgunnine

The major pyrimidines

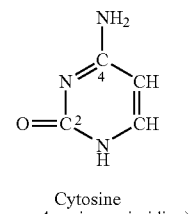
Cytosine
(2-oxy-4-aminopyrimidine)

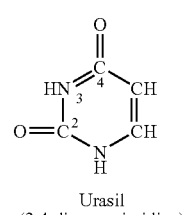
Urasil
(2,4-dioxypyrimidine)

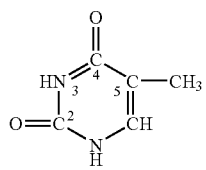
Thymine
(5-methyl-2,4-dioxypyrimidine)

Two minor pyrimidines

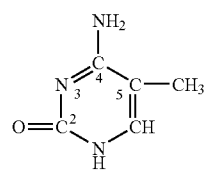
5-Methylcytosine

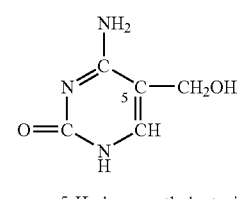
5-Hydroxymethylcytosine

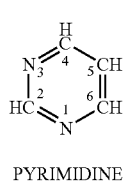
PYRIMIDINE

PURINE

The major ribonucleotides and deoxyribonucleotides.

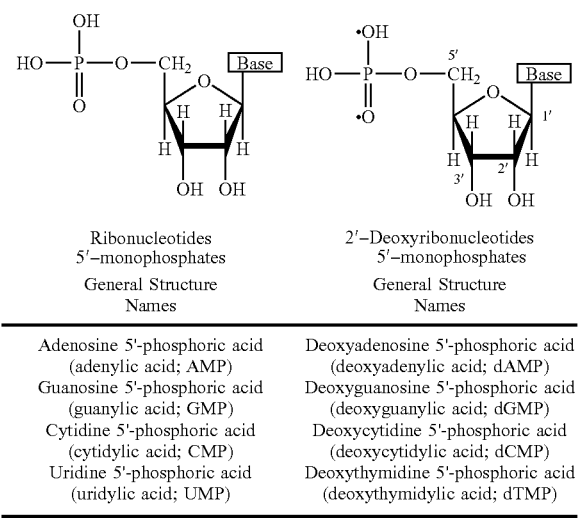

| Ribonucleotides 5′-monophosphates General Structure Names | 2′-Deoxyribonucleotides 5′-monophosphates General Structure Names |
|---|---|
| Adenosine 5′-phosphoric acid (adenylic acid; AMP) | Deoxyadenosine 5′-phosphoric acid (deoxyadenylic acid; dAMP) |
| Guanosine 5′-phosphoric acid (guanylic acid; GMP) | Deoxyguanosine 5′-phosphoric acid (deoxyguanylic acid; dGMP) |
| Cytidine 5′-phosphoric acid (cytidylic acid; CMP) | Deoxycytidine 5′-phosphoric acid (deoxycytidylic acid; dCMP) |
| Uridine 5′-phosphoric acid (uridylic acid; UMP) | Deoxythymidine 5′-phosphoric acid (deoxythymidylic acid; dTMP) |

The special nucleotides in accordance with this invention, as indicated hereinabove, in addition to the P, S and B moieties (PM, SM, and BASE, respectively), include a chemical moiety Sig coavalently attached to the P, S and/or B moieties (PM, SM, and BASE, respectively). Of special interest in accordance with the practices of this invention would be those nucleotides having the general formula, P—S—B-Sig (PM-SM-BASE-Sig) wherein P (PM) is the phosphoric acid moiety including mono-, di-, tri-, or tetraphosphate, S (SM) the sugar or monosaccharide moiety, B the base moiety (BASE), either a purine or a pyrimidine. The phosphoric acid moiety P (PM) is attached at the 3′and/or the 5′position of the S moiety (SM) when the nucleotide is a deoxyribonucleotide and at the 2′, 3′ and/or 5′ position when the nucleotide is a ribonucleotide. The base B moiety (BASE) is attached from the N1 position or the N9 position to the 1′ position of the S moiety (SM) when the base moiety is a pyrimidine or a purine, respectively. The Sig moiety is covalently attached to the B moiety (BASE) of the nucleotide and when so attached is capable of signalling itself or makes itself self-detecting or its presence known and desirably or preferably permits the incorporation of the resulting nucleotide P—S—B-Sig (PM-SM-BASE-Sig) into or to form a double-stranded helical DNA or RNA or DNA-RNA hybrid and/or to be detectable thereon.

Another special nucleotide in accordance with this invention is characterized by the general formula:

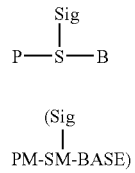

Such nucleotides in accordance with this invention would be characterized as ribonucleotides. The phosphoric acid moiety (PM) is attached at the 2′, 3′ and/or 5′ position of the sugar S moiety (SM) and the base B (BASE) being attached from the N1 position or the N9 position to the 1′ position of the sugar S moiety (SM) when said base (BASE) is a pyrimidine or a purine, respectively. The Sig chemical moiety is covalently attached to the sugar S moiety (SM) and said Sig chemical moiety when attached to said S moiety (SM) is capable of signalling itself or making itself self-detecting or its presence known and preferably permits the incorporation of the ribonucleotide into its corresponding double-stranded RNA or a DNA-RNA hybrid.

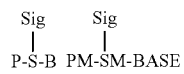

Such nucleotides P—S—B PM-SM-BASE desirably have the Sig chemical moiety attached to the C2′ position of the S moiety (SM) or the C3′ position of the S moiety (SM).

Still further, nucleotides in accordance with the practices of this invention include the nucleotides having the formula,

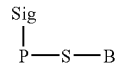

wherein P (PM) is the phosphoric acid moiety, S the sugar moiety (SM)and B (BASE) the base moiety. In these special nucleotides the P moiety (PM) is attached to the 3′ and/or the 5′ position of the S moiety (SM) when the nucleotide is deoxyribonucleotide and at the 2′, 3′ and/or 5′ position when the nucleotide is a ribonucleotide. The base B (B) is either a purine or a pyrimidine and the B moiety (BASE)is attached from the N1 or the N9 position to the 1′ position of the sugar moiety when said B moiety (BASE) is a pyrimidine or a purine, respectively. The Sig chemical moiety is covalently attached to the phosphoric acid P moiety (PM) via the chemical linkage

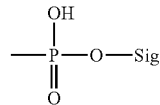

said Sig, when attached to said P moiety (PM) being capable of signalling itself or making itself self-detecting or its presence known and desirably the nucleotide is capable of being incorporated into a double-stranded polynucleotide, such as DNA, RNA or DNA-RNA hybrid and when so incorporated therein is still self-detecting.

It is pointed out that the special nucleotides in accordance with the practices of this invention described or defined hereinabove by the general formula P—S—B-Sig (PM-SM-BASE-Sig), also include nucleotides wherein the Sig chemical moiety is covalently attached to the B moiety (BASE) at the $N^6$ or 6-amino group position when the B moiety (BASE) is adenine or the $N^2$ or 2-amino group position when the B moiety (BASE) is guanine or the $N^4$ or 4-amino group position when the B moiety is cytosine. The resulting nucleotides containing the Sig moiety attached thereto are capable of signalling themselves or making themselves self-detecting or their presence known and being detectable is a double-stranded or DNA, RNA or DNA-RNA hybrid.

By way of summary, as indicated hereinabove with respect to the make-up of the various special nucleotides in accordance with this invention, the special nucleotides can be described as comprising a phosphoric acid moiety P (PM), a sugar moiety S (SM) and a base moiety B (BASE), a purine or pyrimidine, which combination of P—S—B (PM-SM-BASE) is well known with respect to and defines nucleotides, both deoxyribonucleotides and ribonucleotides. The nucleotides are then modified in accordance with the practices of this invention by having covalently attached thereto to the P moiety (PM) and/or the S moiety (SM) and/or the B moiety (BASE), a chemical moiety Sig. The chemical moiety Sig so attached to the nucleotide P—S—B (PM-SM-BASE) is capable of rendering or making the resulting nucleotide, now comprising P—S—B (PM-SM-BASE) with the Sig moiety being attached to one or more of the other moieties, self-detecting or signalling itself or capable of making its presence known per se, when incorporated into a polynucleotide, especially a double-stranded polynucleotide, such as a double-stranded DNA, a double-stranded RNA or a double-stranded DNA-RNA hybrid. The Sig moiety desirably should not interfere with the capability of the nucleotide to form a double-stranded polynucleotide containing the special Sig-containing nucleotide in accordance with this invention and, when so incorporated therein, the Sig-containing nucleotide is capable of detection, localization or observation.

The Sig moiety employed in the make-up of the special nucleotides of this invention could comprise an enzyme or enzymic material, such as alkaline phosphatase, glucose oxidase, horseradish peroxidase, ribonuclease, acid phosphotase or β-galactosidase. The Sig moiety could also contain a fluorescing component, such as fluorescein or rhodamine or dansyl. If desired, the Sig moiety could include a magnetic component associated or attached thereto, such as a magnetic oxide or magnetic iron oxide, which would make the nucleotide or polynucleotide containing such a magnetic-containing Sig moiety detectable by magnetic means. The Sig moiety might also include an electron dense component, such as ferritin, so as to be available by observation. The Sig moiety could also include a radioactive isotope component, such as radioactive cobalt, making the resulting nucleotide observable by radiation detecting means. The Sig moiety could also include a hapten component or per se be capable of complexing with an antibody specific thereto. Most usefully, the Sig moiety is a polysaccharide or oligosaccharide or monosaccharide, which is capable of complexing with or being attached to a sugar or polysaccharide binding protein, such as a lectin, e.g. Concanavilin A. The Sig component or moiety of the special nucleotides in accordance with this invention could also include a chemiluminescent component.

As indicated in accordance with the practices of this invention, the Sig component could comprise any chemical moiety which is attachable either directly or through a chemical linkage or linker arm to the nucleotide, such as to the base B component (BASE) therein, or the sugar S component (SM) therein, or the phosphoric acid P component (PM) thereof.

The Sig component of the nucleotides in accordance with this invention and the nucleotides and polynucleotides incorporating the nucleotides of this invention containing the Sig component are equivalent to and useful for the same purposes as the nucleotides described in the above-identified U.S. patent application Ser. No. 255,223, now U.S. Pat. No. 4,711,955. More specifically, the chemical moiety A described in U.S. patent application Ser. No. 255,223 is functionally the equivalent of the Sig component or chemical moiety of the special nucleotides of this invention. Accordingly, the Sig component or chemical moiety of nucleotides of this invention can be directly covalently attached to the P, S or B moieties (PM, SM or BASE, respectively) or attached thereto via a chemical linkage or linkage arm as described in U.S. patent application Ser. No. 255,223, as indicated by the dotted line connecting B and A of the nucleotides of U.S. Ser. No. 255,223. The various linker arms or linkages identified in U.S. Ser. No. 255,223 are applicable to and useful in the preparation of the special nucleotides of this invention.

A particularly important and useful aspect of the special nucleotides of this invention is the use of such nucleotides in the preparation of DNA or RNA probes. Such probes would contain a nucleotide sequence substantially matching the DNA or RNA sequence of genetic material to be located and/or identified. The probe would contain one or more of the special nucleotides of this invention. A probe having a desired nucleotide sequence, such as a single-stranded polynucleotide, either DNA or RNA probe, would then be brought into contact with DNA or RNA genetic material to be identified. Upon the localization of the probe and the formation of a double-stranded polynucleotide containing the probe and the matching DNA or RNA material to be identified, the resulting formed double-stranded DNA or RNA-containing material would then be observable and identified. A probe in accordance with this invention may contain substantially any number of nucleotide units, from about 5 nucleotides up to about 500 or more, as may be required. It would appear that 12 matching, preferably consecutive, nucleotide units would be sufficient to effect an identification of most of the DNA or RNA material to be investigated or identified, if the 12 nucleotide sequence of the probe matches a corresponding cooperative sequence in the DNA or RNA material being investigated or to be identified. As indicated, such probes may contain one or more of the special Sig-containing nucleotides in accordance with this invention, preferably at least about one special nucleotide per 5–10 of the nucleotides in the probe.

As indicated hereinabove, various techniques may be employed in the practices of this invention for the incorporation of the special nucleotides of this invention into DNA and related structures. One particularly useful technique referred to hereinabove involves the utilization of terminal transferase for the addition of biotinated dUMP onto the 3'ends of a polypyrimidine or to single-stranded DNA. The resulting product, such as a single-stranded or cloned DNA, which has biotinated dUMP attached to the 3' ends thereof, can be recovered by means of a Sepharose-avidin column wherein the avidin would complex with the biotinated dUMP at the ends of the DNA and be subsequently recovered. In accordance with the practices of this invention hybridization to mRNA could be accomplished in solution and the resulting hybrid recovered via a Sepharose-avidin column and the mRNA recovered therefrom. Similar techniques could be employed to isolate DNA-RNA hybrids. This technique employing terminal transferase for the addition of the special nucleotides in accordance with this invention is widely applicable and the resulting modified nucleotides containing the special nucleotides in accordance with this invention including the special biotinated nucleotides or the special glycosylated nucleotides could be selectively recovered via complexing with avidin upon a Sepharose-avidin column or complexing with a lectin, such as Concanavalin A or a Sepharose-Concanavalin A column.

Illustrative of the practices of this invention, biotinated dUTP was added to the 3' ends of d[pT]$_4$ as well as single and double stranded DNA employing terminal transferase and the resulting product was purified through G-50 Sepharose and separated on a Sepharose-avidin affinity column. It was found that 69% of the d[pT]$_4$ molecules were biotinated and recovered on the Sepharose-avidin column. The results of this experiment established that terminal transferase added biotinated dUMP to the 3' ends of a polypyrimidine.

The detection of nucleic acids to which specific molecules have been covalently attached can be effected through the use of many naturally occurring proteins to which small molecules are known to specifically bind. In this procedure the small molecules are bound to the nucleotide using the allyl amine side chain. These nucleotides are then incorporated into specific nucleic acids using a DNA or RNA polymerase or ligase reaction or a chemical linkage. After annealing this probe with a complementary antiprobe sequence, the presence of the probe is assayed for by the specific binding of the protein to the ligand covalently bound to the probe.

Examples of protein-ligand reactions that are appropriate for this type of detector system include:

1. Enzymes and allosteric effector or modulator molecules. An example of this is the enzyme threonine dehydratase which is a heterotropic enzyme in that the effector molecule, L-isoleucine, is different than the substrate, L-threonine, J. Monod, J. Wyman and J. P. Changeux (1965), *J. Mol. Biol.* 12:88–118.

2. Effector molecules involved in regulation. An example of this is the specific binding of 3',5-cyclic adenosine monophosphate to the cyclic AMP receptor protein, I. Pastan and R. Perlman, *Science* 169:339–344 (1969). Another example is the lactose repressor molecule and the inducer molecules isopropylthiogalactoside or thiomethylgalactoside. These two inducer molecules are called gratuitous inducers in that they are not metabolized by the enzymes they induce, W. Gilbert and B. Muller-Hill, *Proc. Natl. Acad. Sci.* (US), 70:3581–3584, (1973).

3. Hormone receptors and other receptors on the surface of the cell to which organic molecules will specifically bind. An example of this is the epinephrine—epinephrine receptor system in which epinephrine is bound in a steriospecific manner with a high affinity to the receptor. With this system, since the receptor protein is insoluble in water, it will be imbedded in a lipid bilayer structure as for instance a liposome. Suitable detector systems would include specific enzymes or fluorescent molecules inside or within the lipid bilayer.

4. Specific ligand binding proteins included in the transport of small molecules. An example of this is the periplasmic binding proteins of bacteria which have been shown to bind many amino acids, glucose, galactose, ribose and other sugars, Pardee, A. *Science,* 162:632–637, (1968); G. L. Hazelbaur, and J. Adler, *Nature New Bio.* 230: 101–104, (1971).

In the above-mentioned examples the ligand bound to the nucleic acid reacts with a naturally occurring protein. The specificity of this reaction resides in the ligand-binding site of the protein.

One further example of small molecule interaction with naturally occurring proteins involves the specific binding of coenzyme or other prosthetic molecules to enzymes. Examples of such coenzymes include thiamin pyrophosphate, flavine mononucleotide, flavine adenine dinucleotide, nicotinamide adenine dinucleotide, nicotinamide adenine dinucleotide phosphate, coenzyme A, pyridoxyl phosphate, biotin, tetrahydrofolic acid, coenzyme $B_{12}$, lipoic and ascorbic acid. Many of these molecules form covalent linkages with their apoenzymes.

However, some, for example, coenzyme A, coenzyme $B_{12}$ and tetrahydrofolic acid, associate in a non-covalent but specific manner with their cognate apoenzymes. A specific coenzyme-apoenzyme system for use in this system is flavine adenine dinucleotide (FAD) and flavine adenine dinucleotide reductase isolated from *Escherichia coli*. With this system the binding of FAD is sufficiently strong to permit detection.

The special nucleotides of this invention and polynucleotides including such nucleotides, either single-stranded or double-stranded polynucleotides, DNA and/or RNA, comprising the components, phosphoric acid moiety P (PM), the sugar or monosaccharide moiety S (SM), the base moiety B (BASE), a purine or a pyrimidine, and the signalling or self-detecting moiety, Sig, covalently attached to either the P, S or B moieties (PM, SM or BASE), as indicated hereinabove, have many uses and utilities. For example, the nucleotides of this invention and polynucleotides containing the nucleotides of this invention are useful as immune-stimulating agents, as adjuvants in vaccines, as agents for the stimulation or induction from competent cells, such as lymphocytes, for the production of lymphokines, cytokines or cytokinins, interferon or other cellular products.

It is well known that double-stranded poly A:U is a stimulator or inducer for the production of interferon, although weakly so. Similarly, poly I:C is also known as a stimulator or inducing agent for the production of interferon.

The advantage of polynucleotides, such as double-stranded polynucleotides incorporating one or more nucleotides in accordance with this invention is that, in effect, such polynucleotides would be more effective and more powerful inducing or stimulating agents for the production of interferon and related materials from cells. For example, nucleotides in accordance with this invention containing the above-described components P, S, B and Sig (PM, SM, BASE and Sig, respectively), are suitably prepared so that the nucleotides and polynucleotides prepared therefrom are more resistant to nucleases. Similarly, such nucleotides and polynucleotides containing the same and suitably prepared which are more capable of contacting, stimulating and penetrating cellular surfaces or membranes, such as the cellular surfaces or membranes of lymphocytes and other cells so as to stimulate the same for the production of a desired cellular product, such as interferon.

Particularly useful among those special nucleotides in accordance with this invention having the formula P—S—B-Sig (PM-SM-BASE-Sig) and especially useful are those wherein the Sig component is at the 5 position of the pyrimidine or the 7 position of the purine or a deazapurine or the $N^2$ position of guanine or the $N^6$ position of adenine. Such nucleotides and polynucleotides incorporating the same, both single-stranded and double-stranded nucleotides, DNA and/or RNA are prepared in accordance with this invention to provide increased stability with respect to the double-stranded helix of DNA or RNA or DNA-RNA hybrid containing the same. Increased resistance to nucleases is also achievable as well as alterations or favorable changes in the hydrophobic properties or electrical or charge properties of the nucleotides and polynucleotides containing the same. Also, nucleotides and polynucleotides in accordance with this invention are prepared which, when administered to humans, have reduced pyrogenicity or exhibit less other whole body toxic responses. Additionally, the nucleotides and polynucleotides are prepared in accordance with this invention to provide a ligand, such as the component Sig, to which specific polypeptides can combine to create or bring about the formation of RNA complexes. It is seen therefore that the nucleotides of this invention include the P, S, B and Sig components (PM, SM, BASE and Sig) wherein the Sig is covalently attached to either the P, S or B moieties (PM, SM, and BASE, respectively) open up or provide a whole array of chemical agents having special biological effects including therapeutic effects and cytotoxic effects.

The special nucleotides of this invention, including polynucleotides containing these nucleotides, in addition to being stimulating or inducing agents for the production of cellular materials or products, such as interferons, lymphokines and/or cytokines, are also useful for their chemotherapeutic effect and for the preparation of chemotherapeutic agents based thereon but also for their cytotoxic effects and the production of cytotoxic agents based thereon. The moiety Sig attached to the special nucleotides of this invention containing the other moieties or components P, S, B (PM, SM, BASE) provides a site per se for the attachment thereto, the Sig component, of special agents of known chemotherapeutic or cytotoxic effect. Such nucleotides could be introduced or administered to the subject being treated, e.g. human body or animal, so as to be incorporated into the DNA and/or RNA components of the body or cell so as to either interfere with the synthesis of the body or cellular DNA and/or RNA or to attack tumors or to, in effect, kill or otherwise interfere with the growth of undesired cells.

The administration of the nucleotides and/or polynucleotides containing the nucleotides to the body, human body or animal, can be effected by a number of suitable means. Particularly effective would be the intravenous introduction to the body of preparations containing the nucleotides of this invention and a suitable physiologically acceptable carrier or the nucleotides could be administered subcutaneously, transdermally, or intramuscularly or by direct introduction into the site where the chemotherapeutic or cytotoxic effect of the nucleotides is sought or desired to be effective. Not only could desired chemotherapeutic or cytotoxic effects be achieved systemically or locally but also, as indicated hereinabove, the special P, S, B and Sig-containing (PM, SM, BASE and Sig, respectively) nucleotides of this invention, including polynucleotides containing such nucleotides, are useful as immune-stimulating agents and adjuvants therefor. Accordingly, vaccines containing the special nucleotides and polynucleotides in accordance with this invention can be prepared having improved effectiveness and versatility.

Of special interest in the practices of this invention improved polynucleotides incorporating the special nucleotides of this invention are provided as inducers or stimulating agents for the production of interferon. Such polynucletoides would be single-stranded or double-stranded ribonucleotides, dsRNA, having the structures,

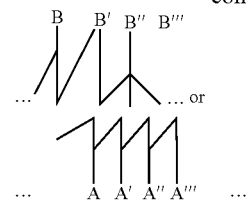

where A and B are complementary base pairs, such as a purine, a 7-deazapurine or pyrimidine modified by the addition of an organic moiety Sig in accordance with the disclosures of this invention on the 5 position of the pyrimidine ring or the 7 position of the purine ring or the $N^2$ of guanine, or the $N^6$ of adenine or the $N^4$ of cytosine as described herein. The modifications of the polynucleotides at these positions lead to relatively undisruptive or non-disruptive double-stranded nucleic acid molecules as measured by rates of association and melting points. In the special polynucleotides of this invention employed as inducers of interferon and other cellular or humoral factors or components, such as lymphokines or cytokines, the following groups would be attached thereto as indicated by the formulas,

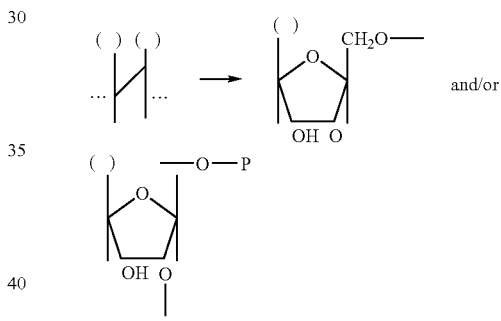

In the utilization of the special polynucleotides of this invention, such as the special dsRNA of this invention in the induction process for the production of interferon it has been demonstrated that DEAE-dextran facilitates this operation. It appears that since DEAE-dextran complexes with dsRNA and protects it for nuclease degradation, thereby enhancing interferon induction. It has also been noted that poly rC:rI is taken into cells more efficiently when complexed with DEAE-dextran. Accordingly in the practices of this invention the hydrophobic properties and the ionic or electron charge properties of the special dsRNA of this invention are important factors and capable of manipulation in the applicability of these materials to induce inteferon production. It has been observed that such conditions or factors which promote the induction of interferon also lead to and promote the induction of other cellular or humoral components, such as lymphokines and cytokines. It is apparent, therefore, that the special nucleotides of this invention act as immune modulators and stimulators of the immune response other than simply being effective as inducers of interferon production. Superior agents for the above in accordance with the practices of this invention would include nucleotides wherein the Sig moiety incorporates biotin or streptavidin or avidin.

Poly rI:poly rC complexed poly L-lysine exhibits adjuvant properties and such properties are enhanced and improved in accordance with the practices of this invention when the poly rI and poly rC components are modified to include one or more of the special nucleotides in accordance with this invention.

The preparation of DNA probes in accordance with another aspect of this invention can be carried out in a manner which does not require the preparation or utilization of the special nucleotides described herein. For example, double-stranded DNA can be reacted with a carcinogen or alkylating agent. After the carcinogen has reacted with or alkylated the double-stranded DNA, the resulting modified DNA is melted to produce a DNA hybridizing probe containing the reaction product of the DNA and the carcinogen or alkylating agent. When thus-modified or reacted DNA is employed as a hybridizing probe, any resulting formed double helix or double-stranded DNA would be assayed or searched out by means of a double antibody technique. The primary antibody would be an anti-carcinogen and the secondary antibody would be horseradish-peroxidase conjugated anti-peroxidase antibody. The advantage of this technique is that it would be easy to label the double-stranded DNA. This special approach is indicated hereinabove in the examples accompanying the description of this invention and is generally applicable for the preparation of DNA probes from double-stranded or double helical DNA. However, this procedure is a disruptive procedure involving the modification of the double helical deoxyribonucleotide polymer or DNA.

In the description of the special nucleotides and modified DNA employed or developed in the practices of this invention, mention has been made of mono, oligo and polysaccharides. It is pointed out that derivatives of mono, oligo and polysaccharides are also useful in the preparation of the special nucleotides of this invention. For example, it is possible to modify individual sugar moieties employed in the make-up of the special nucleotides and employ the resulting modified sugar moieties to effect or carry-out additional chemical reactions. Such modified mono, oligo and polysaccharide moieties, when employed as the Sig moiety in the preparation of the special nucleotides of this invention, provide an added versatility with respect to the detection of the nucleotides or other compounds containing such modified saccharides either as the sugar S (SM) or as the Sig moiety thereof.

In another aspect of this invention the Sig moiety instead of being attached to a nucleotide could also be attached to proteins. Not only could such proteins be attached to nucleotides or polynucleotides but also such proteins could be identified per se whether attached to a nucleotide or polynucleotide or unattached. In accordance with the practices of this aspect of the invention, a suitable such protein adduct would have the formula,

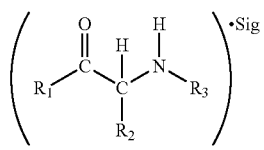

wherein $R_1$ is an OH or an amino acid or acids $R_2$ is an amino acid side chain and $R_3$ is H or an amino acid or acids and Sig is attached to the $R_1$ and/or $R_2$ and/or $R_3$.

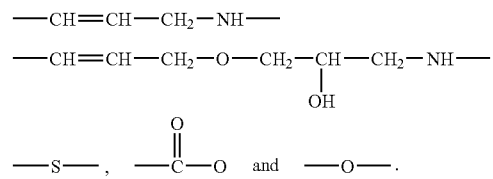

What is claimed is:

1. A nucleotide having the formula

wherein PM is a phosphate moiety, SM is a sugar moiety comprising a pentose sugar selected from a ribose or a deoxyribose, and BASE is a pyrimidine, purine or 7-deazapurine moiety, said PM being covalently attached to the C2' or the C3' or the C5' position of SM, said BASE being covalently attached to the 1' position of SM from the $N^1$ position when BASE is a pyrimidine or the $N^9$ position when BASE is a purine or 7-deazapurine, and said Sig is covalently attached to the C2' or the C3' or the C5' position of SM directly or through a linkage group and Sig is a moiety which is detectable when said nucleotide is incorporated into a double-stranded nucleic acid duplex.

2. The nucleotide in accordance with claim 1, comprising a deoxyribonucleotide or a dideoxyribonucleotide.

3. The nucleotide in accordance with claim 1 comprising a ribonucleotide.

4. The nucleotide in accordance with claim 1 wherein Sig comprises a moiety containing at least 3 carbon atoms.

5. The nucleotide in accordance with claim 1 wherein Sig is selected from the group consisting of monosaccharides, oligosaccharides and polysaccharides.

6. The nucleotide in accordance with claim 5 wherein Sig is selected from the group consisting of triose, tetrose, pantose, hexose, heptose and octose.

7. The nucleotide in accordance with claim 1 wherein Sig includes a glycosidic linkage moiety.

8. The nucleotide in accordance with claim 1 wherein Sig comprises a sugar residue and said sugar residue is complexed with a binding protein therefor.

9. The nucleotide in accordance with claim 8 wherein said binding protein comprises a lectin.

10. The nucleotide in accordance with claim 9 wherein said lectin comprises Concanavalin A.

11. The nucleotide in accordance with claim 1 wherein Sig comprises a component selected from the group consisting of biotin, iminobiotin, an electron dense component, a magnetic component, an enzyme, a hormone component, a radioactive component, a metal-containing component, a fluorescent component, a chemiluminescent component, an antigen, a hapten and an antibody component.

12. The nucleotide in accordance with claim 11 wherein said electron dense component comprises ferritin.

13. The nucleotide in accordance with claim 9 wherein said lectin is conjugated to ferritin.

14. The nucleotide in accordance with claim 10 wherein said Concanavalin A is conjugated to ferritin.

15. The nucleotide in accordance with claim 11 wherein Sig comprises a radioactive isotope.

16. The nucleotide in accordance with claim 15 wherein said radioactive isotope comprises radioactive cobalt.

17. The nucleotide in accordance with claim 11 wherein Sig comprises an enzyme.

18. The nucleotide in accordance with claim 17 wherein said enzyme is selected from the group consisting of alkaline phosphatase, acid phosphatase, β-galactosidase, ribonuclease, glucose oxidase and peroxidase.

19. The nucleotide in accordance with claim 11 wherein Sig comprises a fluorescent component.

20. The nucleotide in accordance with claim 19 wherein said fluorescent component is selected from the group consisting of fluorescein, rhodamine and dansyl.

21. The nucleotide in accordance with claim 11 wherein said Sig comprises a magnetic component.

22. The nucleotide in accordance with claim 21 wherein said magnetic component comprises a magnetic oxide.

23. The nucleotide in accordance with claim 22 wherein such magnetic oxide comprises ferric oxide.

24. The nucleotide in accordance with claim 23 wherein Sig includes a hapten component capable of complexing with an antibody specific thereto.

25. The nucleotide in accordance with claim 1 wherein Sig includes a catalytic metal-containing component.

26. A composition comprising at least one nucleotide in accordance with claim 1, a polypeptide capable of forming a complex with Sig, and a moiety which can be detected when such complex is formed.

27. The composition in accordance with claim 26 wherein said polypeptide comprises a polylysine.

28. The composition in accordance with claim 26 wherein said polypeptide comprises at least one member selected from the group consisting of avidin, streptavidin and anti-Sig immunoglobulin.

29. The composition in accordance with claim 26 wherein Sig comprises a ligand and said polypeptide comprises an antibody thereto.

30. The composition in accordance with claim 26 wherein said detectable moiety is selected from the group consisting of biotin, iminobiotin, an electron dense component, a magnetic component, an enzyme, a hormone component, a radioactive component, a chemiluminescent component, an antigen, a hapten and an antibody component.

31. The nucleotide in accordance with claim 3 wherein said Sig comprises a moiety which is detectable when said deoxyribonucleotide or said dideoxyribonucleotide is incorporated with, contained in or associated with an oligo- or polynucleotide.

32. The nucleotide in accordance with claim 4 wherein said Sig comprises a moiety which is detectable when said ribonucleotide is incorporated with, contained in or associated with an oligo- or polynucleotide.

33. The nucleotide of claim 1 wherein said chemical linkage comprises or includes an olefinic bond at the ∂-position relative to P, or any of the moieties: